United States Patent
Horenstein et al.

(10) Patent No.: US 10,662,191 B2
(45) Date of Patent: May 26, 2020

(54) NICOTINIC ACETYLCHOLINE RECEPTOR SILENT AGONISTS

(71) Applicant: University of Florida Research Foundation, Inc., Gainesville, FL (US)

(72) Inventors: Nicole Alana Horenstein, High Springs, FL (US); Roger Lee Papke, Gainesville, FL (US); Marta Quadri, Vigano (IT)

(73) Assignee: UNIVERSITY OF FLORIDA RESEARCH FOUNDATION INC., Gainesville, FL (US)

( * ) Notice: Subject to any disclaimer, the term of this patent is extended or adjusted under 35 U.S.C. 154(b) by 0 days.

(21) Appl. No.: 15/768,175

(22) PCT Filed: Oct. 14, 2016

(86) PCT No.: PCT/US2016/057024
§ 371 (c)(1),
(2) Date: Apr. 13, 2018

(87) PCT Pub. No.: WO2017/066558
PCT Pub. Date: Apr. 20, 2017

(65) Prior Publication Data
US 2018/0298002 A1    Oct. 18, 2018

Related U.S. Application Data

(60) Provisional application No. 62/241,885, filed on Oct. 15, 2015.

(51) Int. Cl.
| | |
|---|---|
| *C07D 471/10* | (2006.01) |
| *C07D 211/58* | (2006.01) |
| *C07D 211/70* | (2006.01) |
| *C07D 295/037* | (2006.01) |
| *C07D 295/073* | (2006.01) |
| *C07D 295/155* | (2006.01) |
| *A61K 31/495* | (2006.01) |
| *A61K 31/499* | (2006.01) |
| *A61K 31/452* | (2006.01) |
| *A61K 31/42* | (2006.01) |
| *C07D 295/096* | (2006.01) |

(52) U.S. Cl.
CPC ........... *C07D 471/10* (2013.01); *A61K 31/42* (2013.01); *A61K 31/452* (2013.01); *A61K 31/495* (2013.01); *A61K 31/499* (2013.01); *C07D 211/58* (2013.01); *C07D 211/70* (2013.01); *C07D 295/037* (2013.01); *C07D 295/073* (2013.01); *C07D 295/096* (2013.01); *C07D 295/155* (2013.01)

(58) Field of Classification Search
CPC .. C07D 471/10; C07D 211/58; C07D 211/70; C07D 295/037; C07D 295/073; C07D 295/155
See application file for complete search history.

(56) References Cited

U.S. PATENT DOCUMENTS

| | | | | |
|---|---|---|---|---|
| 8,039,459 B2 * | 10/2011 | Cormier | ............. | A61K 31/4439 514/183 |
| 2009/0325929 A1 | 12/2009 | Li et al. | | |
| 2013/0137697 A1 | 5/2013 | Papke et al. | | |

FOREIGN PATENT DOCUMENTS

WO    WO2009071326 A2    6/2009

OTHER PUBLICATIONS

Li et al., J. Cardiovasc Pharmacol, vol. 59, No. 6, Jun. 2012, 507-513.*
International Search Report and Written Opinion for PCT/US2016/057024 dated Jan. 13, 2017.
Papke, et al. (2014) "The Minimal Pharmacophore for Silent Agonism of the a7 Nicotinic Acetylcholine Receptor", J. Pharmacol. Exp. Ther. 350: 665-680.
Briggs, et al. (2009) "Role of channel activation in cognitive enhancement mediated by a7 nicotinic acetylecholine receptors", British J. Pharma. 158: 1486-1494.
Balant et al., Prodrugs for the improvement of drug absorption via different routes of administration, European Journal of Drug Metabolism and Pharmacokinetics, (1990), 15(2): 143-153.
Balimane et al., Involvement of multiple transporters in the oral absorption of nucleoside analogues, Advanced Drug Delivery Reviews, 39 (1999): 183-209.
Chojnacka et al., Synthesis and evaluation of a conditionally-silent agonist for the α7 nicotinic acetylcholine receptor, Bioorganic & Medicinal Chemistry Letters 23 (2013): 4145-4149.
Didier M. Lambert, Rationale and applications of lipids as prodrug carriers, European Journal of Pharmaceutical Sciences,11 Suppl 2(2000): S15-S27.
Fleisher et al., Design of prodrugs for improved gastrointestinal absorption by intestinal enzyme targeting, Methods in Enzymology, (1985)112: 360-381.
Han et al., Targeted prodrug design to optimize drug delivery, AAPS Pharmsci 2000 2(1) article 6 (http://www.pharmsci.org/): 1-11.
Mandana Asgharnejad, Improving Oral Drug Transport Via Prodrugs, Transport Processes in Pharmaceutical Systems, (2000): 185-218.
Ma et al., Mild Method for Ullmann Coupling Reaction of Amines and Aryl Halides, Organic Letters, 2003, 5(14): 2453-2455.
Matteoli et al., A distinct vagal anti-inflammatory pathway modulates intestinal muscularis resident macrophages independent of the spleen, Neurogastroenterology (2014) 63: 938-948.

(Continued)

*Primary Examiner* — Rebecca L Anderson
(74) *Attorney, Agent, or Firm* — Thomas | Horstemeyer, LLP

(57) ABSTRACT

Derivatives of N,N-diethyl-N'-phenyl-piperazine, a silent agonist of the mammalian α7 nicotinic acetylcholine receptor, are provided. These silent agonists control the desensitization state of the receptor. Further provided are pharmaceutical compositions that allow the administration of the silent agonists of the disclosure to a subject animal or human in need of treatment for a pathological condition arising from such as inflammation. The novel silent agonists also may be co-administered to a patient simultaneously or consecutively with a type II positive allosteric modulator to modulate the activity of the receptor.

4 Claims, 12 Drawing Sheets

(56) References Cited

OTHER PUBLICATIONS

Papke et al., Comparative pharmacology of rat and human α7 nAChR conducted with net charge analysis, British Journal of Pharmacology (2002) 137: 49-61.

Papke et al., The correction of alpha7 nicotinic acetylcholine receptor concentration-response relationships in Xenopus oocytes, Neuroscience Lettters 256 (1998): 163-166.

Papke et al., The analgesic-like properties of the alpha7 nAChR silent agonist NS6740 is associated with non-conducting conformations of the receptor, Neuropharmacology (2015) 91: 34-42.

Roger L. Papke, Estimation of both the potency and efficacy of α7 nAChR agonists from single-concentration responses, Life Sciences 78 (2006): 2812-2819.

Parrish et al., Modulation of TNF Release by Choline Requires α7 Subunit Nicotinic Acetylcholine Receptor-Mediated Signaling, Mol. Med. 14(9-10)(2008): 568-574.

Pauletti et al., Improvement of oral peptide bioavailability: Peptidomimetics and Prodrug Strategies, Advanced Drug Delivery Reviews 27 (1997): 235-256.

Miroslav Pohanka, Alpha7 Nictonic Acetylcholine Receptor is a Target in Pharmacology and Toxicology, International Journal of Molecular Sciences (2012)13: 2219-2238.

Rosas-Ballina et al., The Selective α7 Agonist GTS-21 Attenuates Cytokine Production in Human Whole Blood and Human Monocytes Activated by Ligands for TLR2, TLR3, TLR4, TLR9, and RAGE, Mol. Med. 15(7-8)(2009): 195-202.

Y. Sadzuka, Effective prodrug liposome and conversion to active metabolite, Current Drug Metabolism (2000) 1:31-48.

Saeed et al., Cholinergic stimulation blocks endothelial cell activation and leukocyte recruitment during inflammation, The Journal of Experimental Medicine, 201(7)(2005): 1113-1123.

Thomsen et al., The α7 Nicotinic acetylcholine receptor ligands methyllycaconitine, NS6740 and GTS-21 reduce lipopolysaccharide-induced TNF-α release from microglia, Journal of Neuroimmunology 251 (2012): 65-72.

Kevin J. Tracey, Physiology and immunology of the cholinergic antiinflammatory pathway, The Journal of Clinical Investigation 117(2)(2007): 289-296.

Uteshev et al., Activation and inhibition of native neuronal alpha-bungarotoxin-sensitive nicotinic ACh receptors, Brain Research 948(2002): 33-46.

Van Maanen et al., Two Novel α7 Nicotinic Acetylcholine Receptor Ligands: In Vitro Properties and Their Efficacy in Collagen-Induced Arthritis in Mice, PLOS One (2015) 10: 1-20.

Wang et al., Nicotinic acetylcholine receptor α7 subunit is an essential regulator of inflammation, Nature 421(2003): 384-388.

Williams et al., The effective opening of nicotinic acetylcholine receptors with single agonist binding sites, The Journal of General Physiology, (2011) 137: 369-384.

Zhang et al., Amino Acid Promoted CuI-Catalyzed C—N Bond Formation between Aryl Halides and Amines or N-Containing Heterocycles, J. Org. Chem. (2005) 70: 5164-5173.

Zhou et al., Fluorine Bonding—How Does It Work in Protein-Ligand Interactions? J. Chem. Inf. Model (2009) 49: 2344-2355.

Bagdas et al., The α7 nicotinic receptor dual allosteric agonist and positive allosteric modulator GAT 107 reverses nociception in mouse models of inflammatory and neuropathic pain, British Journal of Pharmacology (2016) 173: 2506-2520.

Donvito et al., The interaction between alpha 7 nicotinic acetylcholine receptor and nuclear peroxisome proliferator-activated receptor-$\alpha$ represents a new antinociceptive signaling pathway in mice, Experimental Neurology 295 (2017): 194-201.

Hone et al., Nicotinic acetylcholine receptors in neuropathic and inflammatory pain, FEBS Letters 592 (2018): 1045-1062.

Donald B. Hoover, Cholinergic modulation of the immune system presents new approaches for treating inflammation, Pharmacology & Therapeutics 179 (2017) 1-16.

Horenstein et al., Anti-inflammatory Silent Agonists, ACS Medicial Chemistry Letters 2017 (8) 989-991.

King et al., A G protein-coupled α7 nicotinic receptor regulates signaling and TNF-α release in microglia, FEBS Open Bio 7 (2017) 1350-1361.

Papke, et al., The Minimal Pharmacophore for Silent Agonism of the α7 Nicotinic Acetylcholine Receptor, The Journal of Pharmacology and Experimental Therapeutics, (2014) 350: 665-680.

Papke et al., Persistent activation of α7 nicotinic ACh receptors associated with stable induction of different desensitized states, British Journal of Pharmacology (2018) 175: 1838-1854.

Peng et al., Multiple Modes of α7 nAChR Noncompetitive Antagonism of Control Agonist-Evoked and Allosterically Enhanced Currents, Molecular Pharmacology, (2013) 84: 459-475.

Quadri et al., Dissection of N,N-diethyl-N'-phenylpiperazines as α7 nicotinic receptor silent agonists, Bioorg Med Chem. Jan. 15, 2016; 24(2): 286-293.

Quadri et al., Identification of α7 Nicotinic Acetylcholine Receptor Silent Agonists Based on the Spirocyclic Quinuclidine-D2-Isoxazoline Scaffold: Synthesis and Electrophysiological Evaluation, ChemMedChem 2017(12): 1335-1348.

Quadri et al., Sulfonium as a surrogate for Ammonium: A new α7 nicotinic acetylcholine receptor partial agonist with desensitizing activity, J Med Chem. 2017; 60(18): 7928-7934.

Srivastva, Bioreversible Phosphate Protective Groups: Synthesis and Stability of Model Acyloxymethyl Phosphates, Bioorganic Chemistry (1984) 12, 118-129.

Stokes et al., Looking below the surface of nicotinic acetylcholine receptors, Trends Pharmacol Sci. 2015; 36(8): 514-523.

\* cited by examiner

NICOTINIC ACETYLCHOLINE RECEPTOR SILENT AGONISTS

CROSS-REFERENCE TO RELATED APPLICATION

This application is the 35 U.S.C. § 371 national stage application of PCT Application No. PCT/US2016/057024, filed Oct. 14, 2016, where the PCT claims priority to U.S. Provisional Application No. 62/241,885, entitled "DISSECTION OF N,N-DIETHYL-N'-PHENYLPIPERAZINES AS NICOTINIC RECEPTOR SILENT AGONISTS" filed on Oct. 15, 2015, the entireties of which are herein incorporated by reference.

STATEMENT REGARDING FEDERALLY SPONSORED RESEARCH OR DEVELOPMENT

This invention was made with Government support under Grant No. GM057481 awarded by the National Institutes of Health. The Government has certain rights in the invention.

TECHNICAL FIELD

The present disclosure is generally related to nicotinic acetylcholine receptor silent agonists. The present disclosure is also generally related to the use of the nicotinic acetylcholine receptor silent agonists in therapeutic compositions for treating inflammatory disorders.

BACKGROUND

The homopentameric a7 nicotinic acetylcholine receptor (nAChR) is a ligand-gated ion channel (Papke, R. L. (2014) *Biochem. Pharmacol.*) characterized by a unique form of concentration-dependent rapid desensitization (Papke, & Papke (2002) *Br. J. Pharm.* 137: 49-61; Papke & Thinschmidt (1998) *Neurosci. Let.* 256: 163-166). The receptor belongs to the large superfamily of ligand-gated ion channels (Papke, R. L. (2014) *Biochem. Pharmacol.*) that are all characterized by a disulfide-constrained "Cys-loop", which is thought to be involved in the conformational changes linking ligand binding and ion channel activation.

Nicotinic acetylcholine receptors (nAChRs) are validated therapeutic targets for several pathologies of the central and peripheral nervous system including Alzheimer's and Parkinson's diseases, addiction disorders, schizophrenia, pain management, and inflammation-mediated processes. Recent reports have provided evidence for expression of this receptor subtype in non-neuronal cells including lymphocytes, macrophages, and intestinal and lung endothelial and epithelial cells (Parrish et al., (2008) *Mol. Med.* 14: 567-574; Rosas-Ballina et al., (2009) *Mol. Med.* 15: 195-202; Al-Wadei et al., (2012) *Mol. Cancer Res.* 10: 239-249; Matteoli et al., (2014) *Gut* 63: 938-948), indicating a non-synaptic role for the receptor. Moreover, α7 is a key part of the cholinergic anti-inflammatory response (Wang et al., (2003) *Nature* 421: 384-388) in which levels of pro-inflammatory cytokines are decreased (Tracey, K. J. (2007) *J. Clin. Invest.* 117: 289-296), making this receptor of great interest considering the wide range of diseases in which systemic inflammation is present.

Further, nicotine and other αagonists (Saeed et al., (2005) *J. Exp. Med.* 201: 1113-1123) have been effective in models of inflammation, inhibiting local leukocyte recruitment and reducing endothelial cell activation, implicating α7 nAChR involvement in regulation of inflammatory processes. All these data makes the α7 receptor a promising drug target for the treatment of several neurological disorders including inflammatory diseases and chronic pain. Notably, anti-inflammatory effects has been associated with desensitized, non-conducting states of the receptor (Thomsen & Mikkelsen (2012) *J. Neuroimmunol.* 251: 65-72; Papke et al., (2015) *NeuroPharm.* 91: 34-42). Thus, compounds that are able to selectively place the receptor into a desensitized state rather than act as partial agonists are of considerable interest (Papke et al., (2015) *NeuroPharm.* 91: 34-42). For the α7 receptor two distinct desensitized states have been identified (Williams et al., (2011) *Mol. Pharmacol.* 80: 1013-1032). They differ in being sensitive ($D_s$) or insensitive (Di) to conversion to open states by a type II PAM. Silent agonists are desensitizing compounds that have been identified and designed to selectively induce the $D_s$ state in the α7 nAChR with extremely low or absent partial agonist activity. The archetype compound 1,4-diazabicyclo[3.2.2]nonan-4-yl(5-(3-(trifluoromethyl) phenyl) furan-2-yl) methanone (NS6740), lacking in the ability to generate an α7 ion current, is an example of a silent agonist associated with anti-inflammatory activity; however, even the simple tetraethyl ammonium cation is a silent agonist for the α7 nAChR (Papke et al., (2015) *NeuroPharm.* 91: 34-42; Chojnacka et al., (2013) *Bioorg. Med. Chem. Lett.* 23: 4145-4149).

It was recently reported that the compound N,N-diethyl-N'-phenyl piperazine (diEPP) (Papke et al., (2014) *J. Pharmacol. Experimental Therap.* 350: 665-680) is also active as a silent agonist, and it has a structure that lends itself well to functionalization to explore the potential for further enhancement and control of silent agonist activity.

SUMMARY

The structure of the N,N-diethyl-N'-phenyl piperazine (diEPP) framework was modified in three ways: different substituents on the phenyl ring, based on the identity of the functional groups and their position, the nature of the linkage between the two rings to test the essentiality of the N-aryl linkage, and generated monoethyl tertiary amine analogs of diEPP to test if a hard positive charge at the quaternary nitrogen was required for silent agonism.

Briefly described, one aspect of the disclosure encompasses embodiments of a compound having the formula I, II, III, or IV:

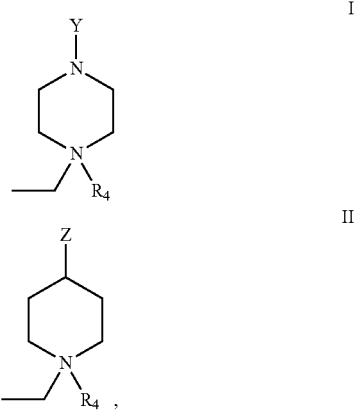

-continued

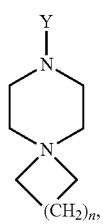

III

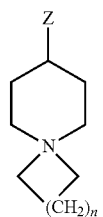

IV or a pharmaceutically acceptable salt thereof, wherein:
Y can be

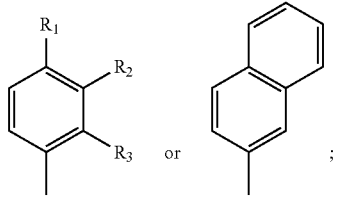

Z can be

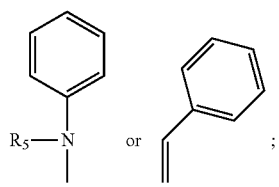

n can be 1, 2, 3, or 4; $R_1$, $R_2$, and $R_3$ can each be independently a hydrogen, an alkyl group, cyano, an alkoxy group, a halogen, a trihaloalkyl, a carboxamide, pentafluorosulfanyl, or hydroxyl, and wherein the halogen is fluorine, chlorine or bromine; $R_4$ can be a hydrogen or an ethyl group; and $R_5$ can be a hydrogen or a carboxytrifluoromethyl.

In some embodiments of this aspect of the disclosure, $R_1$, $R_2$, and $R_3$ can each be independently a hydrogen, a methyl, cyano, methoxy, a halogen, trihaloalkyl, a carboxamide or hydroxyl.

In some embodiments of this aspect of the disclosure, $R_1$, $R_2$, and $R_3$ can each be independently a hydrogen, a methyl, cyano, methoxy, a halogen, a trihaloalkyl, a carboxamide or hydroxyl, and $R_5$ is hydrogen.

In some embodiments of this aspect of the disclosure, when $R_1$ is a methyl or a CN, $R_2$ and $R_3$ are each hydrogen; when $R_1$ is a methoxy, $R_2$ is hydrogen $R_3$ is hydrogen or methoxy; when $R_1$ is a halogen, $R_2$ and $R_3$ are each hydrogen; when $R_1$ is a trifluoromethyl, $R_2$ and $R_3$ are each hydrogen; when $R_1$ is a carboxamide, pentafluorosulfanyl, $R_2$ and $R_3$ are each hydrogen; when $R_1$ and $R_3$ are each hydrogen, $R_2$ is a methyl, a CN, a methoxy, a halogen, a trifluoromethyl, or a carboxamide, or OH; when $R_1$ and $R_2$ are each hydrogen, $R_3$ is a methyl or Cl; and $R_4$ is an ethyl group.

Another aspect of the disclosure encompasses embodiments of a pharmaceutical composition comprising a compound having the formula I, II, III, or IV:

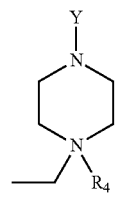

I

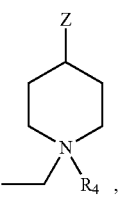

II

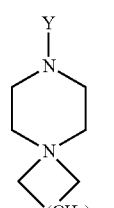

III

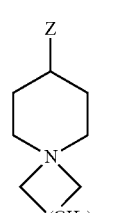

IV or a pharmaceutically acceptable salt thereof, wherein:
Y can be:

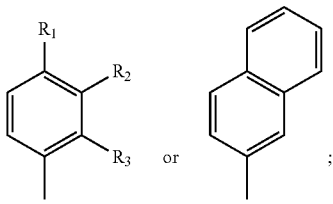

Z can be

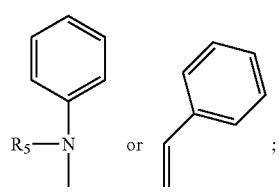

n can be 1, 2, 3, or 4; $R_1$, $R_2$, and $R_3$ can each be independently a hydrogen, an alkyl group, cyano, an alkoxy group, a halogen, a trihaloalkyl, a carboxamide, pentafluorosulfanyl, or hydroxyl, and wherein the halogen is fluorine, chlorine or bromine; $R_4$ can be a hydrogen or an ethyl group; and $R_5$ can be a hydrogen or a carboxytrifluoromethyl; and a pharmaceutically acceptable carrier.

In some embodiments of this aspect of the disclosure, $R_1$, $R_2$, and $R_3$ can each be independently a hydrogen, a methyl, cyano, methoxy, a halogen, trihaloalkyl, a carboxamide, pentafluorosulfanyl, or hydroxyl.

In some embodiments of this aspect of the disclosure, $R_1$, $R_2$, and $R_3$ can each be independently a hydrogen, a methyl, cyano, methoxy, a halogen, a trihaloalkyl, a carboxamide, pentafluorosulfanyl, or hydroxyl, and $R_5$ is hydrogen.

In some embodiments of this aspect of the disclosure, when $R_1$ is a methyl or a CN, $R_2$ and $R_3$ are each hydrogen; when $R_1$ is a methoxy, $R_2$ is hydrogen $R_3$ is hydrogen or methoxy; when $R_1$ is a halogen, $R_2$ and $R_3$ are each hydrogen; when $R_1$ is a trifluoromethyl, $R_2$ and $R_3$ are each hydrogen; when $R_1$ is a carboxamide, pentafluorosulfanyl, $R_2$ and $R_3$ are each hydrogen; when $R_1$ and $R_3$ are each hydrogen, $R_2$ is a methyl, a CN, a methoxy, a halogen, a trifluoromethyl, or a carboxamide, or OH; when $R_1$ and $R_2$ are each hydrogen, $R_3$ is a methyl or Cl; and $R_4$ is an ethyl group.

In some embodiments of this aspect of the disclosure, the composition can be formulated to deliver to a human or animal subject in need thereof, an amount of the compound effective in modulating the activity of a nicotinic acetylcholine receptor in the recipient patient, and wherein the effective amount can delivered as a single dose or as a series of doses.

In some embodiments of this aspect of the disclosure, the nicotinic acetylcholine receptor positive allosteric modulator (PAM) can be a type II PAM.

In some embodiments of this aspect of the disclosure, the nicotinic acetylcholine receptor positive allosteric modulator (PAM) can be the type II PAM 1-(5-chloro-2,4-dimethoxyphenyl)-3-(5-methylisoxazol-3-yl)urea (PNU-120596).

Yet another aspect of the disclosure encompasses a method of modulating the activity of a nicotinic acetylcholine receptor in an animal or human subject by administering to said subject effective doses of a silent agonist of the nicotinic acetylcholine receptor and a nicotinic acetylcholine receptor positive allosteric modulator (PAM).

In some embodiments of this aspect of the disclosure, the silent agonist of the nicotinic acetylcholine receptor and the nicotinic acetylcholine receptor positive allosteric modulator (PAM) can be administered to the subject simultaneously or as consecutive doses.

In some embodiments of this aspect of the disclosure, the silent agonist of the nicotinic acetylcholine receptor is a compound having the formula I, II, III, or IV:

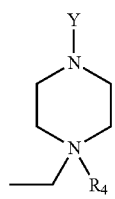

I

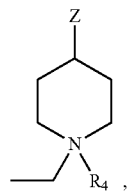

II

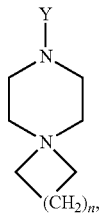

III

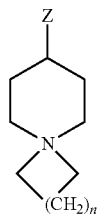

IV or a pharmaceutically acceptable salt thereof, wherein Y is:

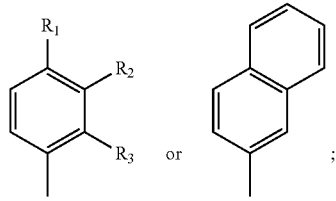

Z is

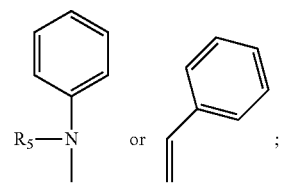

n can be 1, 2, 3, or 4; $R_1$, $R_2$, and $R_3$ can each be independently a hydrogen, an alkyl group, cyano, an alkoxy group, a halogen, a trihaloalkyl, a carboxamide, pentafluorosulfanyl, or hydroxyl, and wherein the halogen is fluorine, chlorine or bromine; $R_4$ is a hydrogen or an ethyl group; and $R_5$ is a hydrogen or a carboxytrifluoromethyl.

In some embodiments of this aspect of the disclosure, the nicotinic acetylcholine receptor positive allosteric modulator (PAM) can be a type II PAM.

In some embodiments of this aspect of the disclosure, the nicotinic acetylcholine receptor positive allosteric modulator (PAM) can be the type II PAM 1-(5-chloro-2,4-dimethoxyphenyl)-3-(5-methylisoxazol-3-yl)urea (PNU-120596).

BRIEF DESCRIPTION OF THE DRAWINGS

Further aspects of the present disclosure will be more readily appreciated upon review of the detailed description of its various embodiments, described below, when taken in conjunction with the accompanying drawings.

FIG. 4A is a graph illustrating the data for the meta-substituted compounds 2.

FIG. 4B is a graph illustrating the data for the para-substituted compounds 2.

FIG. 4C is a graph illustrating the data for selected compounds 1 (left side) and compounds 6 and 8 (right side).

DETAILED DESCRIPTION

Figure 1:
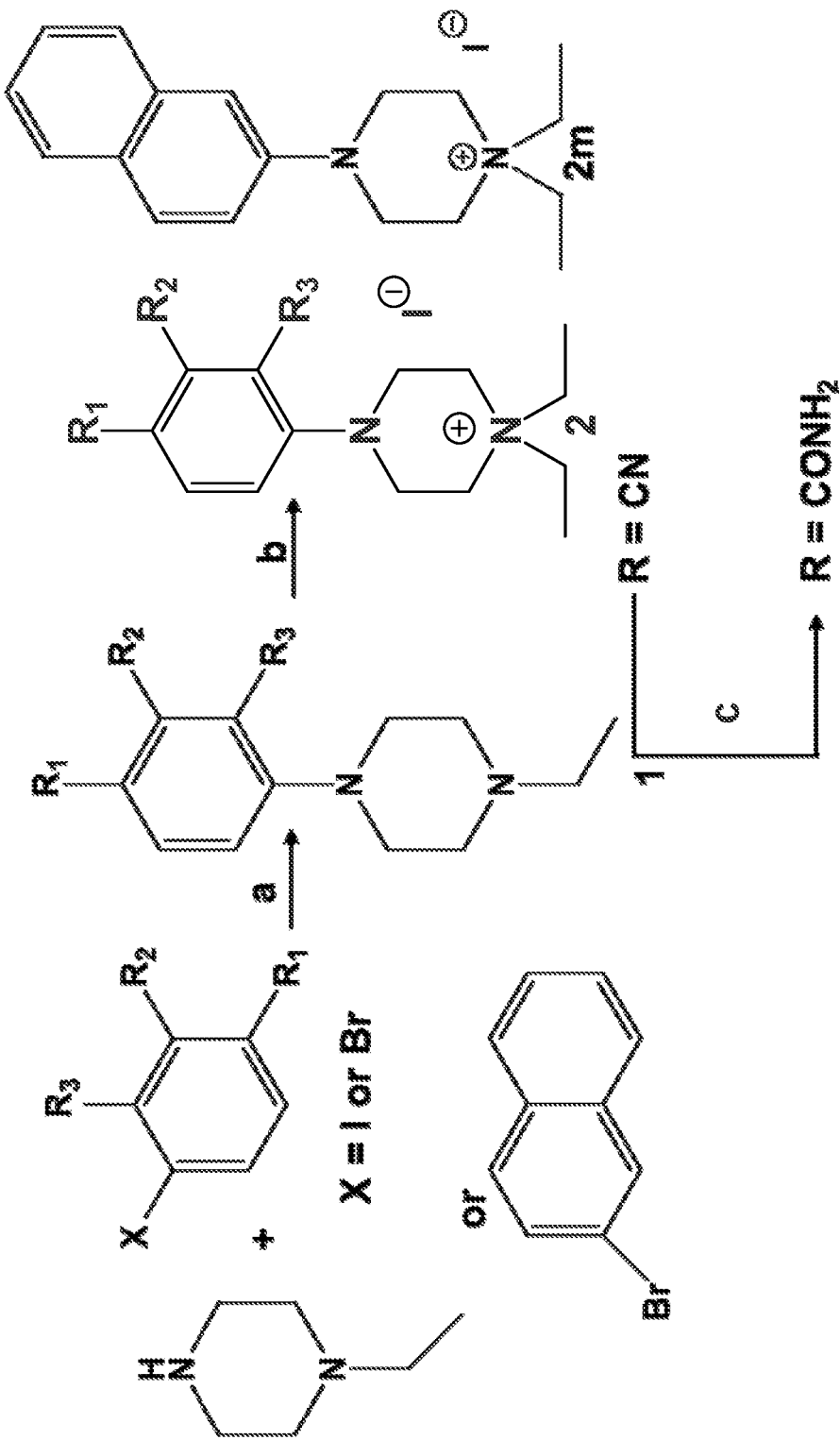
FIG. 1 schematically illustrates a synthetic approach to compounds 1 and 2. Reagents and reaction conditions: (a) 2 equivalents of $K_2CO_3$ (X=I) or $K_2PO_4$ (X=Br), 0.2 equivalent of proline, 0.1 equivalents of CuI, DMSO, 90-100° C., 14 h to 112.5 h; (b) 7 equivalents of EtI, THF, 80-90° C., 17 h to 68.5 h; (c) 2 equivalents of acetaldoxime, 0.05 equivalents of $Pd(PPH_3)_4$, EtOH, reflux, 63 h to 87 h.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein.

Prior to describing the various embodiments, the following definitions are provided and should be used unless otherwise indicated.

Abbreviations nAChR, nicotinic acetylcholine receptor; diEPP, N,N-diethyl-N'-phenyl-piperazine, PAM, positive allosteric modulator, PAM; i.p., intraperitoneal Definitions The term "nicotinic acetylcholine receptors (nAChRs)" as used herein refers to pentameric integral membrane proteins that are members of a family of ligand-gated ion channel receptors, which include the $GABA_A$, glycine, and serotonin $5HT3_A$ and $_B$ receptors.

The nAChRs mediate "fast" synaptic transmission on a millisecond time frame, rapidly changing the membrane potential. Each of the five constituent receptor polypeptide subunits share a common motif that includes a large extracellular N-terminal hydrophilic domain, three transmembrane hydrophobic domains (termed M1-M3), an intracellular loop of variable size that contains consensus sequences of amino acids for enzymatic phosphorylation, and a C-terminal M4 transmembrane hydrophobic domain; the M2 transmembrane domains of each of the five receptor polypeptide subunits are aligned to create a potential channel, whose opening is gated by acetylcholine. These receptors are assembled from an extensive family of subunits. In vertebrates, the 17 nAChR subunits ($\alpha 1$-$\alpha 10$, $\beta 1$-$\beta 4$, $\gamma$, $\delta$, and $\epsilon$) can assemble into a variety of pharmacologically distinct receptor subtypes. There are muscle-type nAChRs and neuronal nAChRs. There is considerable diversity among the sub-family of neuronal nAChRs.

The term "alkoxy" as used herein refers to a linear or branched oxy-containing radical having an alkyl portion of one to about ten carbon atoms, such as a methoxy radical, which may be substituted. In aspects of the disclosure an alkoxy radical may comprise about 1-10, 1-8, 1-6 or 1-3 carbon atoms. In embodiments of the disclosure, an alkoxy radical comprises about 1-6 carbon atoms and includes a $C_1$-$C_6$ alkyl-O-radical wherein $C_1$-$C_6$ alkyl has the meaning set out herein. Examples of alkoxy radicals include without limitation methoxy, ethoxy, propoxy, butoxy, isopropoxy and tert-butoxy alkyls. An "alkoxy" radical may, optionally be substituted with one or more substituents disclosed herein including alkyl atoms to provide "alkylalkoxy" radicals; halo atoms, such as fluoro, chloro or bromo, to provide "haloalkoxy" radicals (e.g. fluoromethoxy, chloromethoxy, trifluoromethoxy, difluoromethoxy, trifluoroethoxy, fluoroethoxy, tetrafluoroethoxy, pentafluoroethoxy, and fluoropropox) and "haloalkoxyalkyl" radicals (e.g. fluoromethoxymethyl, chloromethoxyethyl, trifluoromethoxymethyl, difluoromethoxyethyl, and trifluoroethoxymethyl).

The term "alkyl", either alone or within other terms such as "thioalkyl" and "arylalkyl", as used herein refers to a monovalent, saturated hydrocarbon radical which may be a straight chain (i.e. linear) or a branched chain. An alkyl radical for use in the present disclosure generally comprises from about 1 to 20 carbon atoms, particularly from about 1 to 10, 1 to 8 or 1 to 7, more particularly about 1 to 6 carbon atoms, or 3 to 6. Illustrative alkyl radicals include methyl, ethyl, n-propyl, n-butyl, n-pentyl, n-hexyl, isopropyl, isobutyl, isopentyl, amyl, sec-butyl, tert-butyl, tert-pentyl, n-heptyl, n-octyl, n-nonyl, n-decyl, undecyl, n-dodecyl, n-tetradecyl, pentadecyl, n-hexadecyl, heptadecyl, n-octadecyl, nonadecyl, eicosyl, dosyl, n-tetracosyl, and the like, along with branched variations thereof. In certain aspects of the disclosure an alkyl radical is a $C_1$-$C_6$ lower alkyl comprising or selected from the group consisting of methyl, ethyl, n-propyl, n-butyl, n-pentyl, n-hexyl, isopropyl, isobutyl, isopentyl, amyl, tributyl, sec-butyl, tert-butyl, tert-pentyl, and n-hexyl. An alkyl radical may be optionally substituted with substituents as defined herein at positions that do not significantly interfere with the preparation of compounds of the disclosure and do not significantly reduce the efficacy of the compounds. In certain aspects of the disclosure, an alkyl radical is substituted with one to five substituents including halo, lower alkoxy, lower aliphatic, a substituted lower aliphatic, hydroxy, cyano, nitro, thio, amino, keto, aldehyde, ester, amide, substituted amino, carboxyl, sulfonyl, sulfuryl, sulfenyl, sulfate, sulfoxide, substituted carboxyl, halogenated lower alkyl (e.g. $CF_3$), halogenated lower alkoxy, hydroxycarbonyl, lower alkoxycarbonyl, lower alkylcarbonyloxy, lower alkylcarbonylamino, cycloaliphatic, substituted cycloaliphatic, or aryl (e.g., phenylmethyl benzyl)), heteroaryl (e.g., pyridyl), and heterocyclic (e.g., piperidinyl, morpholinyl). Substituents on an alkyl group may themselves be substituted.

The term "cycloalkyl" as used herein refers to radicals having from about 3 to 8, or 3 to 6 carbon atoms and containing one or two such rings that may be attached in a pendant manner or may be fused. Examples of cycloalkyl groups include single ring structures such as cyclopropyl, cyclobutyl, cyclopentyl, cyclohexyl, cycloheptyl, cyclooctyl, cyclononyl, cyclodecyl, cyclododecyl, and the like.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

The term "carbonyl" as used herein refers to a carbon radical having two of the four covalent bonds shared with an oxygen atom. Carbonyl—The term "carbonyl" as used herein refers to the —(C=O)— group.

The term "carboxamide" as used herein refers to the group —CONH—.

The Term "carboxyl" as used herein refers to the —COOH group.

The terms "co-administration" or "co-administered" as used herein refer to the administration of at least two compounds or agent(s) or therapies to a subject. In some embodiments, the co-administration of two or more agents/ therapies is concurrent. In other embodiments, a first agent/ therapy is administered prior to a second agent/therapy in this aspect, each component may be administered separately, but sufficiently close in time to provide the desired effect, in particular a beneficial, additive, or synergistic effect. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

The term "composition" as used herein refers to a product comprising the specified ingredients in the specified amounts, as well as any product which results, directly or indirectly, from combination of the specified ingredients in the specified amounts. Such a term in relation to a pharmaceutical composition is intended to encompass a product comprising the active ingredient(s), and the inert ingredient(s) that make up the carrier, as well as any product which results, directly or indirectly, from combination, complexation, or aggregation of any two or more of the ingredients, or from dissociation of one or more of the ingredients, or from other types of reactions or interactions of one or more of the ingredients. Accordingly, the pharmaceutical compositions of the present disclosure encompass any composition made by admixing a compound of the present disclosure and a pharmaceutically acceptable carrier.

When a compound of the present disclosure is used contemporaneously with one or more other drugs, a pharmaceutical composition containing such other drugs in addition to the compound of the present disclosure is contemplated. Accordingly, the pharmaceutical compositions of the present disclosure include those that also contain one or more other active ingredients, in addition to a compound of the present disclosure. The weight ratio of the compound of the present disclosure to the second active ingredient may be varied and will depend upon the effective dose of each ingredient. Generally, an effective dose of each will be used. Thus, for example, but not intended to be limiting, when a compound of the present disclosure is combined with another agent, the weight ratio of the compound of the present disclosure to the other agent will generally range from about 1000:1 to about 1:1000, preferably about 200:1 to about 1:200. Combinations of a compound of the present disclosure and other active ingredients will generally also be within the aforementioned range, but in each case, an effective dose of each active ingredient should be used. In such combinations the compound of the present disclosure and other active agents may be administered separately or in conjunction. In addition, the administration of one element may be prior to, concurrent to, or subsequent to the administration of other agent(s).

A therapeutic composition of the disclosure may comprise a carrier, such as one or more of a polymer, carbohydrate, peptide or derivative thereof, which may be directly or indirectly covalently attached to the compound. A carrier may be substituted with substituents described herein including without limitation one or more alkyl, amino, nitro, halogen, thiol, thioalkyl, sulfate, sulfonyl, sulfinyl, sulfoxide, hydroxyl groups. In aspects of the disclosure the carrier is an amino acid including alanine, glycine, praline, methionine, serine, threonine, asparagine, alanyl-alanyl, prolyl-methionyl, or glycyl-glycyl. A carrier can also include a molecule that targets a compound of the disclosure to a particular tissue or organ.

A compound of the disclosure may be in the form of a prodrug that is converted in vivo to an active compound.

Compounds of the disclosure can be prepared using reactions and methods generally known to the person of ordinary skill in the art, having regard to that knowledge and the disclosure of this application including the Examples. The reactions are performed in solvent appropriate to the reagents and materials used and suitable for the reactions being effected. It will be understood by those skilled in the art of organic synthesis that the functionality present on the compounds should be consistent with the proposed reaction steps. This will sometimes require modification of the order of the synthetic steps or selection of one particular process scheme over another in order to obtain a desired compound of the disclosure. It will also be recognized that another major consideration in the development of a synthetic route is the selection of the protecting group used for protection of the reactive functional groups present in the compounds described in this disclosure. An authoritative account describing the many alternatives to the skilled artisan is Greene and Wuts (Protective Groups In Organic Synthesis, Wiley and Sons, 1991).

Compounds of the disclosure which are acidic in nature are capable of forming base salts with various pharmacologically acceptable cations. These salts may be prepared by conventional techniques by treating the corresponding acidic compounds with an aqueous solution containing the desired pharmacologically acceptable cations and then evaporating the resulting solution to dryness, preferably under reduced pressure. Alternatively, they may be prepared by mixing lower alkanolic solutions of the acidic compounds and the desired alkali metal alkoxide together and then evaporating the resulting solution to dryness in the same manner as before. In either case, stoichiometric quantities of reagents are typically employed to ensure completeness of reaction and maximum product yields.

The compounds of the disclosure which are basic in nature can form a wide variety of different salts with various inorganic and organic acids. In practice is it desirable to first isolate a compound of the disclosure from a reaction mixture as a pharmaceutically unacceptable salt and then convert the latter to the free base compound by treatment with an alkaline reagent and subsequently convert the free base to a pharmaceutically acceptable acid addition salt. The acid addition salts of the base compounds of the disclosure are readily prepared by treating the base compound with a substantially equivalent amount of the chosen mineral or inorganic or organic acid in an aqueous solvent medium or in a suitable organic solvent such as methanol or ethanol. Upon careful evaporation of the solvent, the desired solid salt is obtained.

A composition of the disclosure may be sterilized by, for example, filtration through a bacteria retaining filter, addition of sterilizing agents to the composition, irradiation of the composition, or heating the composition. Alternatively, the compounds or compositions of the present disclosure may be provided as sterile solid preparations e.g. lyophilized powder, which are readily dissolved in sterile solvent immediately prior to use.

A compound of the disclosure includes crystalline forms which may exist as polymorphs. Solvates of the compounds formed with water or common organic solvents are also intended to be encompassed within the term. In addition, hydrate forms of the compounds and their salts are encompassed within this disclosure. Further prodrugs of compounds of the disclosure are encompassed within the term.

The term "cyano" as used herein refers to a carbon radical having three of four covalent bonds shared by a nitrogen atom, in particular —CN. A cyano group may be substituted with substituents described herein.

A compound of the disclosure includes derivatives. As used herein the term "derivative" of a compound of the disclosure refers to a chemically modified compound wherein the chemical modification takes place either at a functional group or ring of the compound. Non-limiting examples of derivatives of compounds of the disclosure may include N-acetyl, N-methyl, N-hydroxy groups at any of the available nitrogens in the compound.

A compound of the disclosure can contain one or more asymmetric centers and may give rise to enantiomers, diasteriomers, and other stereoisomeric forms which may be defined in terms of absolute stereochemistry as (R)- or (S)-. Thus, compounds of the disclosure include all possible diasteriomers and enantiomers as well as their racemic and optically pure forms. Optically active (R)- and (S)-isomers may be prepared using chiral synthons or chiral reagents, or resolved using conventional techniques. When a compound of the disclosure contains centers of geometric asymmetry, and unless specified otherwise, it is intended that the compounds include both E and A geometric isomers. All tautomeric forms are also included within the scope of a compound of the disclosure.

The terms "effective amount," "therapeutically-effective amount," and "therapeutically effective dose" as used herein refer to the amount of a compound, material, or composition comprising a compound or composition of the present disclosure, and which is effective for producing a desired therapeutic effect, biological or medicinal response in a tissue system, animal or human that is being sought by a researcher, veterinarian, medical doctor or other clinician, which includes alleviation of the symptoms of the disease or disorder being treated or a reduction in a side-effect due to an administered pharmaceutical agent.

The term "excipient" as used herein refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

The term "halo" as used herein refers to a halogen such as fluorine, chlorine, bromine or iodine atoms.

The term "hydroxyl" as used herein refers to the —OH group.

The term "modulate" refers to the activity of a composition to affect (e.g., to promote or retard) an aspect of cellular function, including, but not limited to, cell growth, proliferation, apoptosis, and the like.

The term "pharmaceutically acceptable carrier" as used herein refers to a diluent, adjuvant, excipient, or vehicle with which a probe of the disclosure is administered and which is approved by a regulatory agency of the Federal or a state government or listed in the U.S. Pharmacopeia or other generally recognized pharmacopeia for use in animals, and more particularly in humans. Such pharmaceutical carriers can be liquids, such as water and oils, including those of petroleum, animal, vegetable or synthetic origin, such as peanut oil, soybean oil, mineral oil, sesame oil and the like. The pharmaceutical carriers can be saline, gum acacia, gelatin, starch paste, talc, keratin, colloidal silica, urea, and the like. When administered to a patient, the probe and pharmaceutically acceptable carriers can be sterile. Water is a useful carrier when the probe is administered intravenously. Saline solutions and aqueous dextrose and glycerol solutions can also be employed as liquid carriers, particularly for injectable solutions. Suitable pharmaceutical carriers also include excipients such as glucose, lactose, sucrose, glycerol monostearate, sodium chloride, glycerol, propylene, glycol, water, ethanol and the like. The present compositions, if desired, can also contain minor amounts of wetting or emulsifying agents, or pH buffering agents. The present compositions advantageously may take the form of solutions, emulsion, sustained-release formulations, or any other form suitable for use.

The compounds of the disclosure may also include "pharmaceutically acceptable salt(s)". By pharmaceutically acceptable salts is meant those salts which are suitable for use in contact with the tissues of a subject or patient without undue toxicity, irritation, allergic response and the like, and are commensurate with a reasonable benefit/risk ratio. Pharmaceutically acceptable salts are described for example, in Berge, et al., *J. Pharmaceut. Sci.*, 1977, 66: 1. Suitable salts include salts that may be formed where acidic protons in the compounds are capable of reacting with inorganic or organic bases. Suitable inorganic salts include those formed with alkali metals, e.g. sodium and potassium, magnesium, calcium, and aluminum. Suitable organic salts include those formed with organic bases such as the amine bases, e.g. ethanolamine, diethanolamine, triethanolamine, trimethamine, N-methylglucamine, and the like. Suitable salts also include acid addition salts formed with inorganic acids (e.g. hydrochloric and hydrobromic acids) and organic acids (e.g. acetic acid, citric acid, maleic acid, and the alkane- and arene-sulfonic acids such as methanesulfonic acid and benzenesulfonic acid). When there are two acidic groups present, a pharmaceutically acceptable salt may be a mono-acid-mono-salt or a di-salt; and similarly where there are more than two acidic groups present, some or all of such groups can be salified.

The term "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "substituted aryl" as used herein includes an aromatic ring, or fused aromatic ring system consisting of no more than three fused rings at least one of which is aromatic, and where at least one of the hydrogen atoms on a ring carbon has been replaced by a halogen, an amino, a hydroxy, a nitro, a thio, an alkyl, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to, hydroxyphenyl, chlorophenyl and the like.

In the event that embodiments of the disclosed compounds in the composition or pharmaceutical composition form salts, these salts are within the scope of the present disclosure. Reference to a compound used in the composition or pharmaceutical composition of any of the formulas herein is understood to include reference to salts thereof, unless otherwise indicated. The term "salt(s)", as employed herein, denotes acidic and/or basic salts formed with inorganic and/or organic acids and bases. In addition, when a compound contains both a basic moiety and an acidic moiety, zwitterions ("inner salts") may be formed and are included within the term "salt(s)" as used herein. Pharmaceutically acceptable (e.g., non-toxic, physiologically acceptable) salts are preferred, although other salts are also useful, e.g., in isolation or purification steps which may be employed during preparation. Salts of the compounds of a compound may be formed, for example, by reacting the compound with an amount of acid or base, such as an equivalent amount, in a medium such as one in which the salt precipitates or in an aqueous medium followed by lyophilization.

Embodiments of the compounds of the composition or pharmaceutical composition of the present disclosure that contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Embodiments of the compounds of the composition or pharmaceutical composition of the present disclosure that contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine, and the like.

Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Solvates of the compounds of the composition or pharmaceutical composition of the present disclosure are also contemplated herein.

To the extent that the disclosed the compounds of the composition or pharmaceutical composition of the present disclosure, and salts thereof, may exist in their tautomeric form, all such tautomeric forms are contemplated herein as part of the present disclosure.

All stereoisomers of the compounds of the composition or pharmaceutical composition of the present disclosure, such as those that may exist due to asymmetric carbons on the various substituents, including enantiomeric forms (which may exist even in the absence of asymmetric carbons) and diastereomeric forms, are contemplated within the scope of this disclosure. Individual stereoisomers of the compounds of the disclosure may, for example, be substantially free of other isomers, or may be admixed, for example, as racemates or with all other, or other selected, stereoisomers. The stereogenic centers of the compounds of the present disclosure can have the S or R configuration as defined by the IUPAC 1974 Recommendations.

The term "prodrug" refers to an inactive precursor of the compounds of the composition or pharmaceutical composition of the present disclosure that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Harper, N.J. (1962). Drug Latentiation in Jucker, ed. Progress in Drug Research, 4:221-294; Morozowich et al. (1977). Application of Physical Organic Principles to Prodrug Design in E. B. Roche ed. Design of Biopharmaceutical Properties through Prodrugs and Analogs, APhA; Acad. Pharm. Sci.; E. B. Roche, ed. (1977). Bioreversible Carriers in Drug in Drug Design, Theory and Application, APhA; H. Bundgaard, ed. (1985) Design of Prodrugs, Elsevier; Wang et al. (1999) Prodrug approaches to the improved delivery of peptide drug, Curr. Pharm. Design. 5(4):265-287; Pauletti et al. (1997). Improvement in peptide bioavailability: Peptidomimetics and Prodrug Strategies, Adv. Drug. Delivery Rev. 27: 235-256; Mizen et al. (1998). The Use of Esters as Prodrugs for Oral Delivery of β-Lactam antibiotics, Pharm. Biotech. 11, 345-365; Gaignault et al. (1996). Designing Prodrugs and Bioprecursors I. Carrier Prodrugs, Pract. Med. Chem. 671-696; M. Asgharnejad (2000). Improving Oral Drug Transport Via Prodrugs, in G. L. Amidon, P. I. Lee and E. M. Topp, Eds., Transport Processes in Pharmaceutical Systems, Marcell Dekker, p. 185-218; Balant et al. (1990) Prodrugs for the improvement of drug absorption via different routes of administration, Eur. J. Drug Metab. Pharmacokinet., 15(2): 143-53; Balimane and Sinko (1999). Involvement of multiple transporters in the oral absorption of nucleoside analogues, Adv. Drug Delivery Rev., 39(1-3):183-209; Browne (1997). Fosphenytoin (Cerebyx), Clin. *Neuropharmacol.* 20(1): 1-12; Bundgaard (1979). Bioreversible derivatization of drugs-principle and applicability to improve the therapeutic effects of drugs, Arch. Pharm. Chemi. 86(1): 1-39; H. Bundgaard, ed. (1985) Design of Prodrugs, New York: Elsevier; Fleisher et al. (1996). Improved oral drug delivery: solubility limitations overcome by the use of prodrugs, Adv. Drug Delivery Rev. 19(2): 115-130; Fleisher et al. (1985). Design of prodrugs for improved gastrointestinal absorption by intestinal enzyme targeting, Methods Enzymol. 112: 360-81; Farquhar D, et al. (1983). Biologically Reversible Phosphate-Protective Groups, J. Pharm. Sci., 72(3): 324-325; Han, H. K. et al. (2000). Targeted prodrug design to optimize drug delivery, AAPS PharmSci., 2(1): E6; Sadzuka Y. (2000). Effective prodrug liposome and conversion to active metabolite, Curr. Drug Metab., 1(1):31-48; D. M. Lambert (2000) Rationale and applications of lipids as prodrug carriers, Eur. J. Pharm. Sci., 11 Suppl 2:S15-27; Wang, W. et al. (1999) Prodrug approaches to the improved delivery of peptide drugs. Curr. Pharm. Des., 5(4):265-87.

The term "administration" refers to introducing an agent of the present disclosure into a host. One preferred route of administration of the agents is oral administration. Another preferred route is intravenous administration. However, any route of administration, such as topical, subcutaneous, peritoneal, intraarterial, inhalation, vaginal, rectal, nasal, introduction into the cerebrospinal fluid, or instillation into body compartments can be used.

The terms "treatment", "treating", and "treat" as used herein refer to acting upon a disease, disorder, or condition with composition or pharmaceutical composition of the present disclosure to reduce or ameliorate the pharmacologic and/or physiologic effects of the disease, disorder, or condition and/or its symptoms. "Treatment," as used herein, covers any treatment of a disease in a host (e.g., a mammal, typically a human or non-human animal of veterinary interest), and includes: (a) reducing the risk of occurrence of the disease in a subject determined to be predisposed to the disease but not yet diagnosed as infected with the disease, (b) impeding the development of the disease, and (c) relieving the disease, i.e., causing regression of the disease and/or relieving one or more disease symptoms. "Treatment" is also meant to encompass delivery of the composition or pharmaceutical composition of the present disclosure to provide a pharmacologic effect, even in the absence of a disease or condition. For example, "treatment" encompasses delivery of the composition or pharmaceutical composition of the present disclosure that provides for enhanced or desirable effects in the subject (e.g., reduction of disease symptoms, etc.).

The terms "host," "subject," "patient," or "organism" as used herein, includes humans and mammals (e.g., mice, rats, pigs, cats, dogs, and horses). Typical hosts to which compounds of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. The term "living host" refers to a host noted above or another organism that is alive. The term "living host" refers to the entire host or organism and not just a part excised (e.g., a liver or other organ) from the living host.

The term "agonist" as used herein refers to a compound or molecule, including but not limited to, peptides, oligopeptides, and small molecules, variants and derivatives thereof that may interact with a receptor of a cell, thereby inducing an increase in a biochemical or physiological activity attributable to the receptor. The agonist may be, but is not limited to, a natural ligand effector of the receptor, an analog or a mimetic and the like thereof.

The term "antagonist" as used herein refers to a compound or molecule, including but not limited to, peptides, oligopeptides, and small molecules, variants and derivatives thereof that may interact with a receptor of a cell, thereby inducing a decrease in a biochemical or physiological activity attributable to the receptor. The agonist may be, but is not limited to, a natural inhibitor of the receptor, an analog or a mimetic and the like thereof.

The terms "subject" and "subject animal or human" as used herein refers to any animal, including a human, to which a composition according to the disclosure may be delivered or administered.

DESCRIPTION

The present disclosure encompasses embodiments of derivatives of N,N-diethyl-N'-phenyl-piperazine (diEPP), the silent agonist of the mammalian α7 nicotinic acetylcholine receptor. These silent agonist can modulate the desensitization states of the nAChR, thus modulating the activity of the receptor.

In particular, the disclosure further encompasses embodiments of pharmaceutical compositions that allow the administration of the silent agonists of the disclosure to a subject animal or human in need of treatment for a pathological condition arising from such as inflammation of the central or peripheral nervous system. The silent agonist may be co-administered either simultaneously or consecutively with a positive allosteric modulators (PAMs). The disclosure further encompasses embodiments of methods of treating a disorder of the central or peripheral nervous system by administering to a patient in need thereof a therapeutically effective amount of the silent agonist, alone or in conjunction with a PAM.

The α7 nicotinic acetylcholine receptor is a target for control of inflammation-related phenomena via compounds that are able to selectively induce desensitized states of the receptor. Compounds that selectively desensitize, without facilitating significant channel activation, are termed "silent agonists" because they can be detected by co-application with type II positive allosteric modulators (PAMs). One example is N,N-diethyl-N'-phenyl-piperazine (diEPP) (Papke et al., (2014) *J. Pharmacol. Experimental Therap.* 350: 665-680).

Ullmann-type aryl amination was used to a synthesized panel of compounds related to diEPP by substitutions at the aryl ring, the linkage between the piperazine and phenyl rings, and the nature of substituents at the quaternary nitrogen of the piperazine ring. Two-electrode voltage clamping of the human α7 nAChR expressed in *Xenopus* oocytes revealed that it was possible to tune the behavior of compounds to show enhanced desensitization without corresponding partial agonist activity such that trifluoromethyl and carboxamide aryl substituents showed 33 to 46-fold larger PAM-dependent net-charge responses, indicating selective partitioning of the ligand-receptor complexes into the desensitized state.

Nicotinic acetylcholine receptors (nAChRs) belong to the four transmembrane domain superfamily of neurotransmitter-gated ion channels and are composed of pentameric combinations, with a high degree of complexity conferred by 10 different alpha (α1-α10) and non-alpha (β1-β4, γ, δ, ε) subunits. The homomeric α7 nAChR is characterized by: great abundancy in the CNS regions (cortex, hippocampus and auditory cortex); a unique form of concentration-dependent rapid desensitization, high permeability to calcium ions and very low probability of channel opening; expression on non-neuronal cells, such as lymphocytes, macrophages, intestinal and lung endothelial and epithelial cells, adipocytes; multiple allosteric sites; different conformational states: a resting closed one with no ion flow through it in absence of an agonist; a very short-lasting cation-permeable open state; a desensitized state when the agonist is bound but the receptor is closed and no activation can occur.

In particular, depending on the agonist nature, residual inhibition or desensitization can be present. Two different desensitized states, namely Ds and Di (sensitive or insensitive to conversion to open states mediated by a type II positive allosteric modulator) are possible and they might involve different intracellular signaling pathways. α7 nAChR and inflammation: Targeting α7 nAChRs represents a viable and promising therapeutic strategy for a broad array of intractable diseases and conditions with inflammatory components. According to preclinical studies, the α7 nAChR is involved in inflammatory processes through modulation of pro-inflammatory cytokines. Indeed, the "cholinergic anti-inflammatory pathway" modulates the immune system through α7 receptors expressed on macrophages and immune cells, down-regulating proinflammatory cytokine synthesis and preventing tissue damage.

Moreover, α7 nAChR modulates inflammatory genes expression in human adipocytes and its expression levels are significantly decreased in obese subjects. Thus, the α7 nAChR represents a useful target to reduce the low-grade chronic inflammation associated with severe human obesity and the subsequent onset of insulin resistance and Type II diabetes.

The development of new drugs with increased efficacy and safety is of great interest since currently-used agents suffer from major adverse effects and/or incomplete pain relief. The development of new α7 anti-inflammatory drugs has been traditionally focused on selective activators. However the best α7 compounds to address treatment of chronic pain and inflammation may not belong to that category. To this end, the α7 receptor activation was investigated by means of silent agonists, which work by involving non-ion conducting states of the receptor.

A new class of compounds named silent agonists has now been discovered (Chojnacka et al., (2013) *Bioorg. Med. Chem. Lett.* 23: 4145-4149). An α7 silent agonist (FIG. 10) is defined as a molecule that: binds at the orthosteric site of the receptor, but it is not able to activate, or only very weakly, the receptor channel opening when used alone, it inhibits an α7 response to Ach, and induces preferentially non-conducting α7 receptor states (Ds or Di), and therefore it appears like an agonist when co-applied with a type II PAM. The type II PAM PNU-120596 (1-(5-chloro-2,4-dimethoxyphenyl)-3-(5-methylisoxazol-3-yl)urea) destabilizes a form of desensitization unique to the α7 receptor subtype, 1 thereby promoting protracted bursts of channel opening, overcoming the very low channel open probability of α7.

Even in absence of the PAM, receptors in the Ds and/or Di states are potential mediators of signal transduction. The idea of α7 signal trasduction independent to ion channel currents is supported by results collected on the silent agonist NS-6740, studied as a modulator of the inflammatory function of microglia. This compound was more efficacious than some agonists (including choline) in suppressing LPS-stimulated secretion of TNF-α in rat cultured microglia; in in vivo mouse pain models showed antinociceptive activity in formalin- and acetic acid-induced nociceptive conditions, and in pain due to the chronic constrictive nerve injury (significantly dose- and time-dependent).

Novel Potential Silent Agonist Derivatives: diEPP Derivatives:

The silent agonist diEPP (1,1-diethyl-4-phenylpiperazin-1-ium) was chosen as model compound. With the aim of improving its potency and establishing new/additional putative interactions within the α7 binding pocket, two sets of new derivatives were designed and synthesized. The first one was obtained by introducing different substituents in various positions of the phenyl ring and the second by replacing the piperazine ring with the piperidine nucleus.

The new synthesized derivatives were tested in electrophysiological assays on *Xenopus* oocytes transfected with human α7 cDNA to assess their functional profile at the α7 nAChR subtype and to study their activity as α7 PAMs or silent agonists.

Potential Silent Agonist Derivatives:

diEPP derivatives synthesized were partial agonists or inactive at the α7 nAChR subtype. diEPP 17, 19, 20 and 21 were the most advantageous silent agonists of the series, producing big responses when co-applied with PNU-120596. Polar interactions have been hypothesized to be the key to silent agonism. diEPP 17 does not activate α3β4 or α4β2 nAChR, but it is a non-competitive antagonist of these receptor subtypes with IC50 values in the range of 10-100 μM. diEPP 19, 20, 21 do not activate α3β4 or α4β2 nAChR, but diEPP 19 and 21 are non-competitive antagonists of these receptor subtypes.

Silent Agonism:

Silent agonists are compounds that do not produce a significant net-charge response of the receptor when applied alone, but do produce a response when co-applied with a PAM such as PNU-120596. While not wishing to be bound by any one theory, it is possible that the bound state of the receptor in complex with a silent agonist is desensitized, as revealed by co-application with a PAM. Compared to the agonist bound state, the silent agonist bound state is destabilized with respect to entry into the conductive O* state (left), and stabilized with respect to entry into the PAM sensitive Ds state (right).

Compound Syntheses:

The general approach used for the synthesis of diEPP derivatives 2 is depicted in Scheme 1 and proceeds in two steps. The key step in the synthesis is a copper-catalyzed Ullmann-type aryl amination (Ma et al., (2003) *Org. Lett.* 5: 2453-2455) promoted and accelerated by the α-amino acid L-proline. Even though N-methylglycine was reported more effective than L-proline, it was also more reactive toward coupling with aryl halides, so L-proline was selected as the ligand (Ma et al., (2003) *Org. Lett.* 5: 2453-2455). The catalytic coupling allowed avoiding typical drawbacks such as stoichiometric amounts of copper reagents and the high costs for palladium catalysts and their phosphine ligands (Zhang et al., (2005) *J. Org. Chem.* 70: 5164-5173). Both electron-rich and electron-deficient aryl halides were successfully coupled with 1-ethylpiperazine at 90° C. in DMSO using 10 mol % CuI and 20 mol % L-proline as the catalytic system (Zhang et al., (2005) *J. Org. Chem.* 70: 5164-5173). Generally, the coupling reactions proceeded smoothly, but the range of yields of this key step was quite wide (from 5 to 83%).

The coupling reaction was found to be inhibited by ortho-substituents (compounds 1h and 1j), presumably due to steric interference within the intermediate addition and eliminations in the copper complex; moreover, aryl iodides gave better yields (52-83%) than aryl bromides (20-64%) discounting the ortho-substituted halides. Though aryl bromides were usually less costly, aryl iodides were therefore first choice whenever possible. Once obtained, the N-phenyl-N'-ethyl piperazines 1 were converted into the quaternary ammonium salts 2 by reacting them with ethyl iodide in tetrahydrofuran and then purified by chromatography and/or recrystallization to afford the final compounds as pure crystalline products (yields ranged from 15-76%). In a few cases, the crystallization resulted in formation of co-crystals between the desired compound and the crystallization solvent, so that solvent was found to be present in the final compound even after prolonged evaporation under vacuum. In two cases, we were unable to recrystallize compounds 2n (p-trifluoromethyl) and 2s (meta-fluoro) despite a broad survey of different solvent systems. The para- and meta-carboxamides 2t and 2u (Table 3) were readily obtained by hydration of the corresponding nitrile diEPP derivatives (2b and 2i) by reacting them with acetaldoxime in the presence of tetrakis Pd(0) as catalyst. In this reaction, acetaldoxime acts as an efficient water donor for delivery to the nitrile. That, together with its commercial availability at low price, and the easy separation of product from the side products (acetonitrile and acetamide), made acetaldoxime the most advantageous reagent for this transformation.

Figure 2:
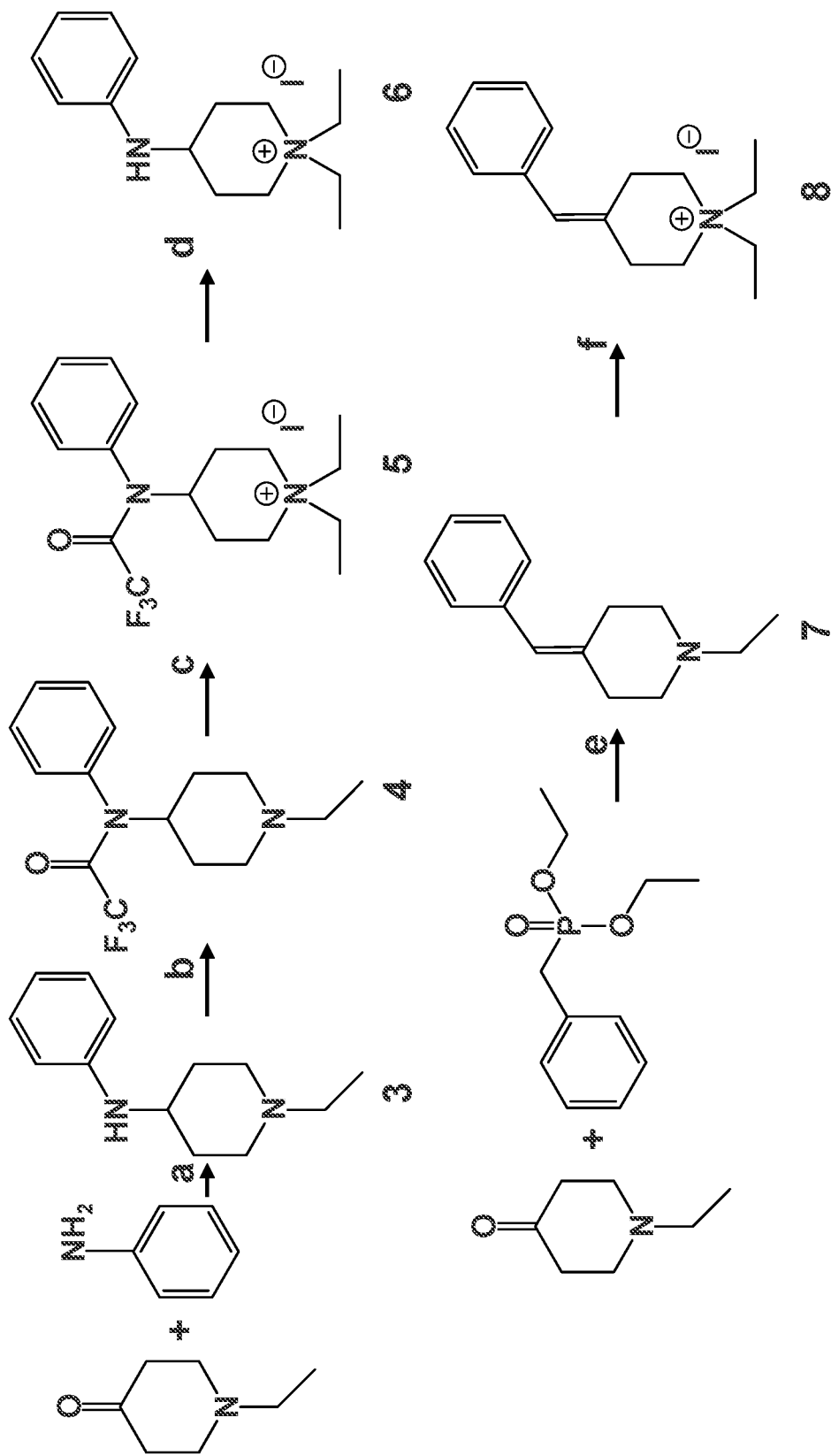
FIG. 2 schematically illustrates a synthetic approach to compounds 6 and 8. Reagents and reaction conditions: (a) 1.2 equivalents of 1-ethyl-4-piperidone, 1 equivalent of aniline, 1.2 equivalents of $NaBH_3CN$, AcOH to pH 6-7, dry MeOH, RT to reflux, 7 d; (b) 3 equivalents of TFAA, 4 equivalents of TEA, dry $CH_2Cl_2$, 0° C., 5 h; (c) 7 equivalents of EtI, copper metal, dry THF, 90° C., 22 h; (d) 12 equivalents of $K_2CO_3$, $MeOH/H_2O$ 7:1, RT, 1 h; (e) 1 equivalent of 1-ethyl-4-piperidone, 1.2 equivalents of diethylbenzylphosphonate, 1.5 equivalents of NaH, 0.2 equivalents of 15-crown-5, dry THF, 0° C. to RT, 4 d; 7 equivalents of EtI, copper metal, EtOH, 90° C., 2 d.

The synthetic routes to diEPP analogues 6 and 8 are shown in FIG. 2. Compound 6, 1,1-diethyl-4-(phenylamino) piperidinium iodide, was synthesized by N-alkylation of the protected reductive amination product of 1-ethyl-4-piperidone with aniline (FIG. 2). The reductive amination proceeded in fair yield (%) as a one-pot reaction in dry methanol/AcOH using sodium cyanoborohydride as reducing agent to afford 3. Complete consumption of the starting materials was not obtained, even after having heated the reaction to reflux. Attempts to optimize the reaction via isolation of the imine intermediate, or use of different anhydrous solvents ($CH_2Cl_2$, toluene, THF), and water-scavenging agents like $MgSO_4$, with or without acetic acid addition to the reaction mixture, were unsuccessful.

Compound 3 was then protected at the aromatic amino group by reaction with trifluoroacetic anhydride in triethylamine in dry dichloromethane at 0° C. Compound 4 was reacted with iodoethane in THF dry to afford the quaternary ammonium corresponding derivative 5, which was then refluxed in a mixture of methanol-water in the presence of potassium carbonate to cleave the trifluoroacetyl protecting group to produce 6. The 4-benzylidine substituted piperidinium salt 8 was obtained after a two-step synthesis. The key step utilized Wittig-Horner reaction of 1-ethyl-4-piperidone and diethyl benzylphosphonate, both commercially available, in the presence of sodium hydride and [15-crown-5] to provide the alkene intermediate 7 in 45% yield. It was found that use of the crown ether in the reaction is important to accelerate the reaction; because omission of the crown ether yielded an incomplete reaction after 3 days.

After purification, the olefinated product was ethylated to the corresponding quaternary ammonium salt (8) by reacting it with iodoethane in dry THF, affording, after careful silica chromatography and recrystallization, the desired final product in 3% yield. This poor yield was attributed to the difficulty in removing an unidentified impurity that, even if present in small amount, co-eluted with the desired product.

Electrophysiology:

The panel of compounds synthesized was assayed using human α7 nAChR expressed in *Xenopus* oocytes and two-electrode voltage clamping. The profile of compound activity is presented in Table 1. The partial agonism activity was evaluated, quantified as net-charge for 30 µM applications of compounds, measured relative to the control response to applications of 60 µM ACh. The induction of PAM-sensitive desensitization was detected as the net-charge responses when compounds were co-applied with the PAM PNU-120596 (30 µM compound+10 µM PNU-120596), measured relative to responses to 60 µM ACh applied alone. It is evident that the diEPP series of compounds 2 (structures, shown in Table 3) exhibit an exceptional sensitivity to the nature and position of the aryl substituent, as evidenced by the broad range of activities against the α7 nAChR, which included partial agonism, varying degrees of silent agonism, and compounds that were effectively inactive, with no agonism and very weak silent agonism.

Figure 3A:
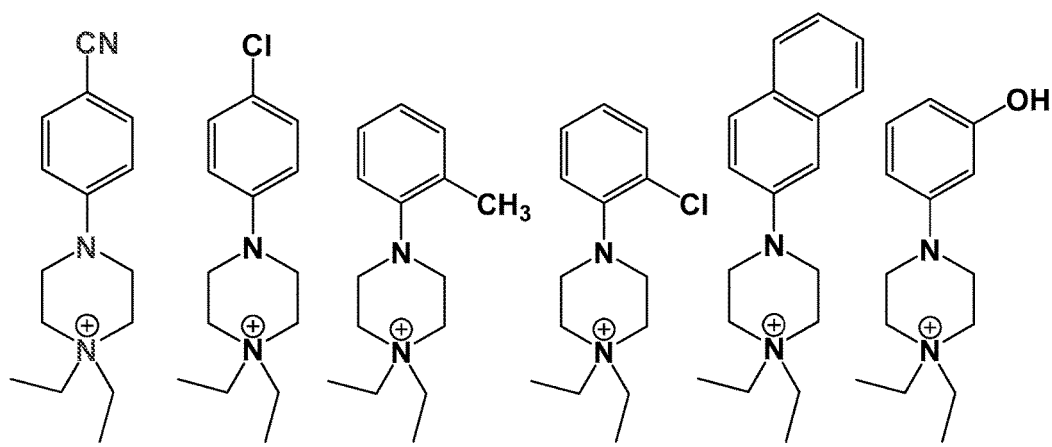
FIG. 3A illustrates the structures of six test compounds that were classified as partial agonists.
Figure 3B:
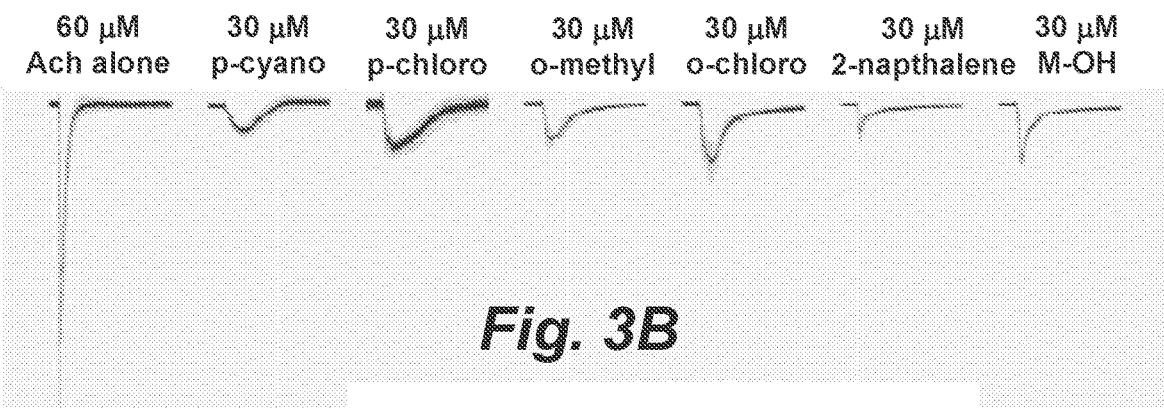
FIG. 3B illustrates the responses of oocytes expressing α7 to the application of the compounds at the probe concentration of 30 μM. In each trace, the black line is the average of the normalized response of at least four cells, and the shaded areas are the range of the standard error of the mean for each point in the averaged traces. The data were obtained at 50 Hz and the traces are each 55 secs in duration (2750 points in each trace). Two control responses to 60 μM ACh were first obtained from each cell for purposes of normalization. The drug-evoked responses were scaled in amplitude to the average of the two ACh-evoked control responses. A representative set of averaged ACh responses are shown on the left to provide scale. Those shown are the ACh responses obtained prior to the application of 30 μM p-cyano. Note that the drug-evoked responses vary in amplitude and also in regard to the ratio of peak currents to net charge (area) calculated relative to the peak and net charge of the ACh controls (Table 2). This ratio is indicative of the drug's potency, i.e. the relationship between the test concentration and EC50 21.

Partial Agonists:

FIG. 3A presents a summary of compounds, o-chloro(2j), o-methyl(2h), m-hydroxy(2k), naphthalene (2m), p-chloro (2e) and p-cyano(2b), that were classified as partial agonists based on their ability to stimulate a net-charge response that was greater than a threshold value of ⅒th the ACh control, when the compounds were applied alone (FIG. 3B). It is a unique property of α7 orthosteric agonist-induced currents that they vary systematically in the relationship between peak current and net charge as a function of the effective concentration applied (Papke & Papke (2002) *Br. J. Pharm.* 137: 49-61; Papke & Thinschmidt (1998) *Neurosci. Let.* 256: 163-166). This was due to the concentration-dependent desensitization of the receptors, which is likely to be associated with high levels of agonist binding site occupancy (Williams et al., (2011) *J. Gen. Physiol.* 137: 369-384) and is observed even when agonists are rapidly applied to small cells (Williams et al., (2012) *Mol. Pharmacol.* 82: 746-759) or acutely dissociated neurons (Uteshev et al., (2002) *Brain Res.* 948: 33-46). The control ACh concentration used for these experiments is roughly the EC80 for the net-charge responses.

By normalizing both the peak currents and net-charge measurements of the drug responses at the probe concentration of 30 µM (FIG. 3B) to those of the ACh control, the relationship between the probe concentration and the EC for each of the drugs was estimated (Papke, R. L. (2005) *Life Sci.*). At a concentration where the ratio of the normalized measures equaled one, the drug would be at the same effective concentration as 60 µM ACh.

As shown in Table 2, the peak-current-to-net-charge ratio for each of the experimental drugs at 30 µM was less than one. Responses to 2m and 2e had the highest peak currents to net charge ratios, indicating that they are the most potent of the drugs tested. The estimated rank potency for the other compounds is given in Table 2. Potency and efficacy can, of course, vary independently. Compounds that that are likely to be relatively potent (based on peak-current-to-net-charge ratios) but produced relatively small net-charge responses at the test concentration are likely to be less efficacious than less potent compounds such as 2h and 2j, which produced larger responses at the test concentration. Based on these considerations, estimated rank efficacies are also provided in Table 2.

Figure 3C:
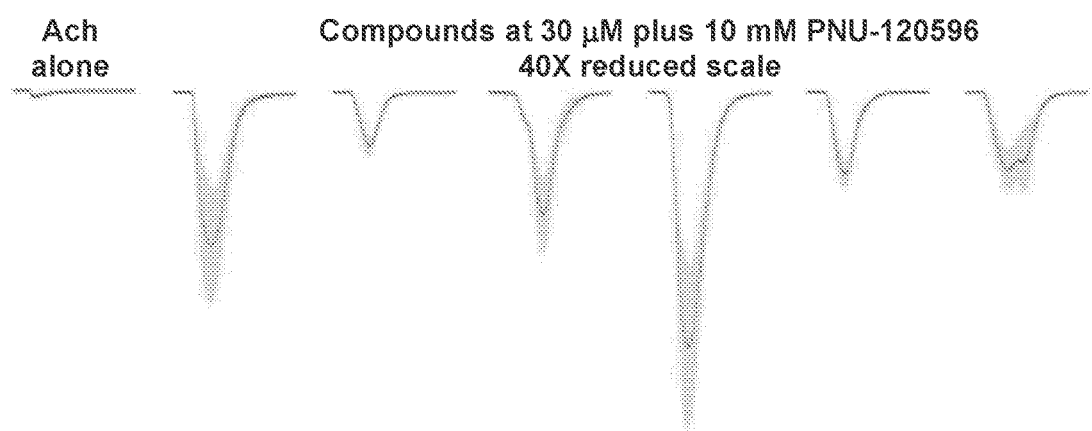
FIG. 3C illustrates the responses of oocytes expressing α7 to the application of the compounds at the probe concentration of 30 μM co-applied with 10 μM 1-(5-chloro-2,4-dimethoxyphenyl)-3-(5-methylisoxazol-3-yl)urea (PNU-120596). Data were normalized and averaged as described for FIG. 3B. For comparison and scale, shown on the left is the averaged ACh response obtained prior to the application of 30 μM p-cyano plus 10 μM PNU-120596. All of the traces are reduced 40-fold relative to those in FIG. 3B.

Of the partial agonists, the ortho-substituted ones showed the highest responses, whether non-polar (Me) or polar (Cl). It is evident that, while these compounds were weak as agonists, their response to application with PNU-120596 was quite strong (FIG. 3C).

Figure 4A:
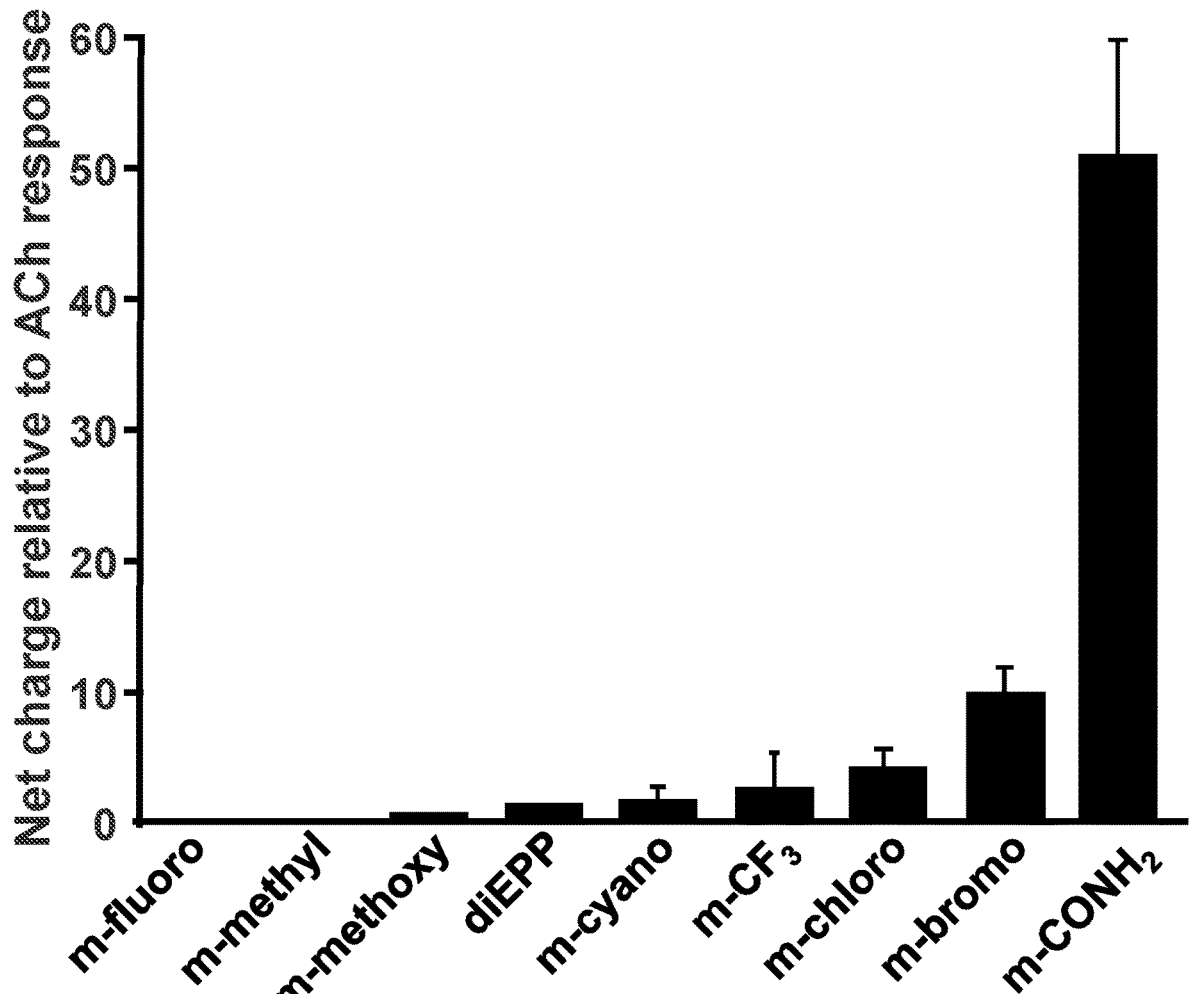
FIGS. 4A-4C illustrate the activity of diEPP compounds and analogs with the α7 nAChR. The left vertical axis refers to the net charge response of compounds when compounds (30 μM) were co-applied with 10 μM PNU-120596, relative to ACh controls. Experimental values are the average of at least 4 independent measurements and the error bars reflect the calculated standard deviation of the mean. In all cases these compounds showed less than 10% of the control ACh response when they were applied alone to the receptor. For reference, all figures include the reference response of diEPP.
Figure 4B:
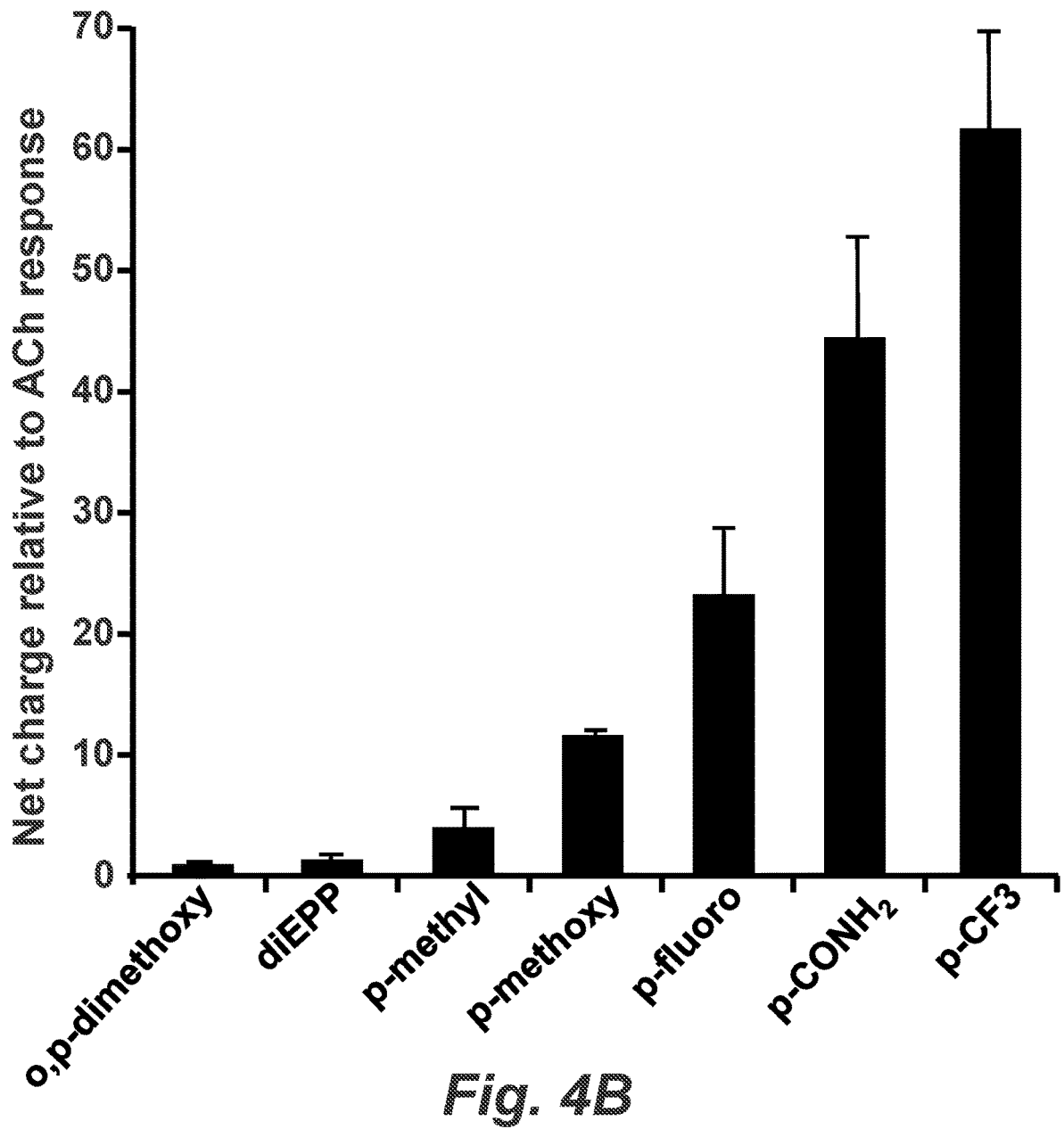

Silent Agonists:

Several substitutions yielded compounds that were candidate silent agonists with little or no partial agonism (i.e. above our detection threshold, but too small for accurate characterization), comparable to, or perhaps slightly greater than the unsubstituted parent diEPP compound (Table 1, and FIGS. 4A-4B 5): m-trifluoromethyl (2o), p-methyl (2a), m-chloro (2f), m-bromo (2p), p-methoxy (2c), p-fluoro (2r), p- and m-carboxamide (2t, 2u), and p-trifluoromethyl (2n). However, four compounds showed no significant activity as either partial agonists or as silent agonists at the concentration tested: m-methoxy (2g), m-methyl (2d), m-fluoro (2s) and m-cyano (2i) derivatives.

Two analogs of diEPP were also prepared (FIG. 2) in which the N-aryl linkage was modified to test the importance of this position. One, compound 6, replaced the piperazine ring with a piperidine ring linked to an aniline group; the other completely eliminated the aniline nitrogen, replacing the aniline group with a benzylidine residue, compound 8 (FIG. 2).

Compounds 6 and 8 both showed enhanced PAM-dependent responses relative to the parent diEPP compound (FIG. 5), suggesting that the nitrogen atom of the N-aryl bond is not essential for silent agonist activity within the diEPP framework.

For some quaternary ammonium diEPP derivatives shown to be silent agonists, the activity of the corresponding tertiary amine was also investigated, i.e. select ethyl phenyl piperazine derivatives, compound 1, Table 3. Specifically, the meta-bromo, meta-chloro, para-trifluoromethyl and para-fluoro compounds (1f, 1p, 1n, 1r) were examined. Interestingly, the tertiary amine 1p (meta-bromo) showed an approximately 5-fold enhanced response relative to diEPP and was only reduced by 0.69-fold relative to its corresponding quaternary salt 2p. This result indicated the hard positive charge is not an absolute requirement for silent agonist activity. With regard to receptor subtype specificity, none of the compounds tested were partial agonists for α3β4, with only one (2g) showing significant antagonism at 100 µM. Select compounds (2p, 2n) were also screened against α4β2 and found neither to be partial agonists nor to have significant antagonist activity at 100 µM.

Other advantageous embodiments of the compositions of the disclosure include 5, 6, and 7 cycloalkyl-piperidines, an example of which, and its synthesis are given in Example 56.

Aryl Substitution Patterns Control State Selectivity:

Hypothetically, an optimized silent agonist, by definition, would be a compound that produced no detectable channel activation, and would exclusively stabilize the receptor into a desensitized state or states that may mediate important forms of signal transduction (Papke et al., (2015) *NeuroPharm.* 91: 34-42; van Maanen et al., (2015) *PLOS ONE* 10: 1-20). It was possible to detect desensitized states (Ds) that are sensitive to, and become conductive when the receptor is treated with a PAM. With this in mind, a compound being a good silent agonist implies that it produces a robust response when co-applied with PNU-120596, and shows little (if any) ability to activate the receptor on its own.

With regard to discerning a pharmacophore for silent agonists, it must be noted that some substituents could have a greater effect on the diminution of agonism, or others might have a greater effect on induction and stabilization of desensitization. In some cases these two effects may work together as is evident by the data shown in FIGS. 3A-3C, where, relative to the parent compound diEPP, some substituents were able to facilitate both a conductive state and a non-conductive Ds state.

Starting from diEPP as the parent compound, through different modifications of the aryl ring, it was possible to obtain several derivatives with enhanced silent agonism profiles (defined as large PAM-dependent currents without increased orthosteric agonism). Among the set of diEPP derivatives generated, the best compounds were meta- or para-substituted diEPP, with small-to-medium size substituent groups, in particular the para-trifluoromethyl, para-fluoro, para- and meta-carboxamide derivatives.

One question was whether a single common property of these functional groups might serve to explain their ability to enhance silent agonism. Fluorine atoms, the trifluoromethyl group, and carboxamides can be quite different in the nature of their interactions with protein binding sites, but in our case they all had enhanced silent agonism behavior compared to the parent compound diEPP, more so than other substituents. To interpret this observation, different atomic properties and atomic interactions were considered. Taking into account the polarity of the group as a primary feature, it is ascribable to fluorine atoms in the first two cases and to the oxygen/amino groups in the latter two. However, not all compounds containing polar groups showed great silent agonism; for example the methoxy and hydroxy derivatives (Table 1), so that polarity on its own is insufficient to explain in a simple way the activity of the best silent agonists. In some cases, fluorine and the trifluoromethyl groups have been considered to enhance lipophilicity (Bohm et al., (2004) *Chembiochem.* 5: 637-643), and if that is the case in our study, introduction of lipophilic substituents such as the methyl group might be expected to improve silent agonism compared to the parent compound diEPP. However, para-methyl and meta-methyl derivatives both failed to effectively induce the Ds state, which supports the idea that polar interactions are operative.

Although hydrogen bonds are well-known to be involved in a myriad of protein-ligand interactions, fluorine rarely participates as a hydrogen-bond acceptor and it would be a weak interaction (Zhou et al., (2009) *J. Chem. Inf. Model* 49: 2344-2355); however, carboxamides are known to be good H-bond acceptors. So if hydrogen bonding was the key interaction behind the silent agonism improvement of those selective compounds compared to diEPP, carboxamide derivatives would show a much greater improvement than the $CF_3$- and F-derivatives, but this was not observed. Thus, the basis for enhanced silent agonism of fluoro, trifluoromethyl, and carboxamide residues may be multifactorial but share in common their ability to stabilize an overall conformational state of the receptor that is desensitized yet sensitive to PNU-120596 through a variety of point-to-point interactions between the various compounds and elements in the silent agonist binding site, considered to be an extension of the site where typical orthosteric agonists such as ACh bind. Intriguing results were observed for the meta-substituted halogen-containing diEPP derivatives, which for the fluoro, chloro, and bromo derivatives showed increasing potentiated responses (Table 1).

To describe these results, halogen bonding interactions were considered. The strength of the interaction increases in the order fluorine<chlorine<bromine<iodine. In our meta-substituted derivatives, an increase in the PAM-dependent currents was observed (FIG. 4A), moving from fluorine (2s; 0.2-fold relative to ACh) hydrogen (diEPP; 1.33-fold) to chlorine (2f; 4.23-fold) to bromine (2p; 9.98-fold), consistent with halogen-bonding interaction with a suitable electron-donor partner in the binding site of the receptor. Indeed, we would predict that electron-rich or electrondonating meta substituents might perform poorly as silent agonists, and this was the case. The meta-methoxy and meta-cyano diEPP (2g, i) derivatives, respectively showed 50% and equivalent PAM-dependent responses compared to the parent unsubstituted diEPP compound. Interestingly, the meta-hydroxy derivative, capable of acting as a hydrogen bond donor, was found to be a partial agonist, suggesting that a unique hydrogen bond at the phenolic OH-group induces a conductive state of the receptor. Chlorine or bromine substitutions in the para or ortho positions do not yield silent agonists, since, in fact, para-chloro, para-bromo and ortho-chloro derivatives showed partial agonist activities with the α7 nAChR subtype (Table 1, FIGS. 3A-3C).

However, in contrast with the trend highlighted among the para-halogen diEPPs, para-fluoro and para-trifluoromethyl diEPP are two of the most active compounds as silent agonists in the diEPP series. The explanation for the divergence in the activity of these para substituents must reside in the unique behavior of fluorine substituents, but this is a complex interplay of numerous effects (Zhou et al., (2009) *J. Chem. Inf. Model* 49: 2344-2355), and in lieu of a high-resolution structure, becomes a speculative endeavor to determine its origin.

Both ortho-chloro and ortho-methyl derivatives are partial agonists of the α7 receptor, and these two substituents have similar Connolly-excluded molecular volumes (14.3 Å versus 16.9 Å), suggesting that a steric directing effect of an ortho-substituent may facilitate entry of the receptor into a conductive state. Yet, the o,p-dimethoxy analogue 21 is not a partial agonist, suggesting that the para-substituent may supersede the putative agonism-promoting effect of an ortho substituent.

The naphthalene derivative (2m) was intended to investigate the tolerance of the binding pocket of the α7 receptor towards more bulky groups, and it became a partial agonist compared to the parent diEPP. These data, compared with the activity of ortho substituted compounds, suggest that the extended point-to-point interactions between the larger naphthalene ligand and receptor are yet another way to induce conductive states of the receptor in addition to the internal conformational biasing or ortho substituents. The relationship between the steric bulk around the core ammonium group as a way to convert partial agonists into silent agonists has been discussed (Papke et al., (2014) *J. Pharmacol. Experimental Therap.* 350: 665-680). Here, substitutions of the aromatic ring are remote from the core ammonium group and do not appear to follow a simple correlation of substituent bulk with silent agonism. Thus, aromatic substituents on diEPP compounds appear to be modulating silent agonism in a different way than simple ammonium compounds do.

Modifications at the Core Piperazine Nitrogen Atoms:

As part of the work to dissect structural features within the diEPP silent agonist pharmacophore, the importance of the nitrogen in the piperazine ring that was attached to the phenyl group was tested and if small modifications at this point in the molecule might enhance silent agonism. Both compounds 6 and 8 were enhanced in terms of their responses when co-applied with PNU-120596, though compound 6 was superior to compound 8 from the point of view of the ratio of the amount of desensitization to residual partial agonism. While we were able to measure currents on application of 8 to α7, application of 6 to α7 resulted in no channel activation within experimental error. Compound 6 thus may serve as a suitable framework for development of cleaner, more state-selective silent agonists.

Figure 4C:
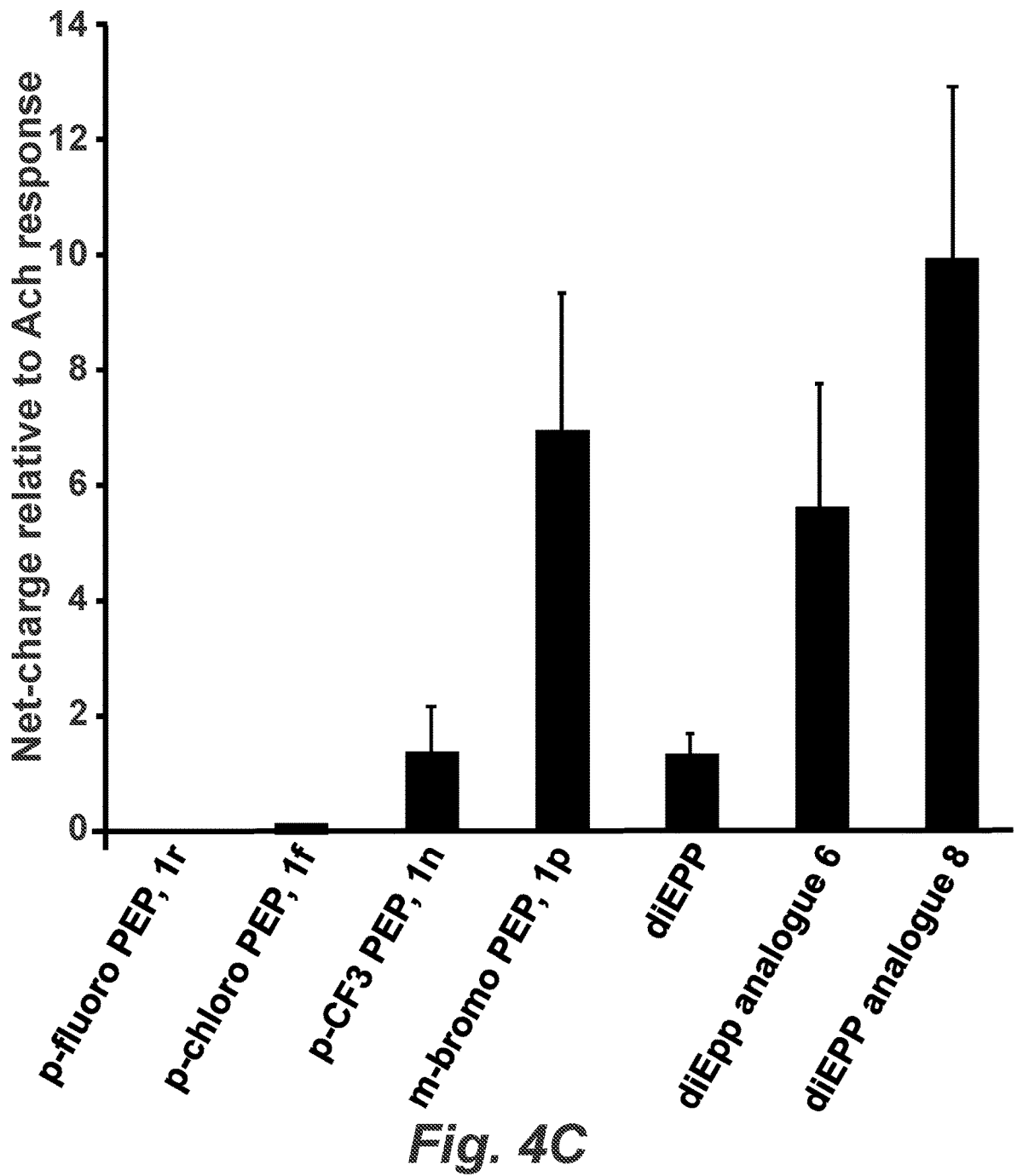

The phenyl ethyl piperazine (PEP) compounds 1f, 1n, 1p, 1r were selected for testing because they correspond to diethylammonium compounds 2 that had significant ability to enter $D_s$ as evidenced by strong PAM co-application responses. It was asked if the hard positive charge present in active compounds 2 was required for silent agonism (FIG. 4C). It was found that, for the most part, these compounds were inactive, with no partial agonism and weak responses to PAM co-application. The exception was meta-bromo PEP 1p, which had a response nearly indistinguishable from the diethyl version 2p (6.9±2.4 vs 10.0±1.7, Table 1). This result provides another indication that the core minimal ammonium pharmacophore observed for simple ammonium compounds may not be required if suitable structural features remote from the core charged nitrogen are present.

This observation is of particular importance for the potential therapeutic development of silent agonists that will be more likely to cross the blood-brain barrier. However, the generally greater activity of the quaternary amines can be exploited for specific indications that would not require brain penetration, such as the targeting of peripheral immune cells for anti-inflammatory activity.

A critical question speaks to the mechanism by which a bound ligand is able to facilitate entry into a desensitized state or states. Available data indicate that silent agonists do not precisely place the receptor into a single desensitized state (Williams et al., (2011) *Mol. Pharmacol.* 80: 1013-1032). Rather, the receptor silent agonist complex is in a highly dynamic series of states; depending on occupancy levels and application time, the complex can enter PAM-insensitive desensitized states (Di), which may evolve over time into PAM-sensitive desensitized states ($D_s$) and or eventually dissociate from the receptor (Papke et al., (2015) *NeuroPharm.* 91: 34-42). Based on the results described here, it is entirely reasonable that a number of different amino acid side chains in the binding site may be utilized as interacting partners for selective entry into a $D_s$ state. Molecular docking studies suggested that multiple binding poses in the orthosteric agonist binding site of the receptor are possible, which leads to a number of hypotheses about specific ligand receptor interactions of interest.

The diEPP molecular framework has been an excellent platform to identify some enhanced silent agonists as well as to identify new molecular features that regulate different features associated with silent agonism. It has been found the p-fluoro and p-trifluoromethyl, and p- and m-carboxamide groups to provide strongly enhanced entry of α7 into the Ds state relative to the parent unsubstituted compound diEPP, and do so with little activity as partial agonists. The limited number of ortho substitutions tested yielded partial agonists. When the para position was substituted with Cl, Br, or cyano, the compounds were partial agonists with strong responses to PAM co-application; however, methoxy, fluoro, carboxamide, and trifluoromethyl substituents had diminished partial agonism and strong PAM co-application responses. The meta position is distinguished from para by the fact that fewer substitutions lead to partial agonism (meta-hydroxyl compound 2k being a noteworthy exception).

The PAM co-application responses were low for most meta-group compounds, with the bromo and carboxamide being standouts for their strong $D_s$ response to PAM application. Interestingly, the nitrogen of the N-aryl linkage is not required for activity, as exemplified by compound 8, indicating the N-aryl functionality is not a critical determinant for stabilizing desensitization. Finally, while three of the four non-quaternary compounds 1 were inactive as silent agonists, the meta-bromo compound 1p showed modest silent agonism with little diminution relative to its ammonium analog 2p, demonstrating that a hard positive charge is not required for activity. These compounds could prove interesting for applications requiring blood brain barrier permeability.

Thus, the Ullman-type couplings used to synthesize the diEPP compounds proved to be versatile for a variety of substituted phenyl halides. Unsurprisingly, couplings of ortho-substituted aryl halides to ethyl piperazine often produced significantly lowered yields. However, because we found that the most effective silent agonists were not ortho-substituted this synthetic limitation had no impact on this study. In the meta series, the most effective silent agonist was the carboxamide-substituted diEPP, with a sharp demarcation from other compounds. In the para series, this demarcation was less sharp, with p-CF3 being most active, closely followed by the p-carboxamide. The para position appears more tolerant of the nature of the substituent. A quaternary center is not absolutely required for silent agonism, as exemplified by compound 1p, bearing a single ethyl group. Compounds 6 and 8 which are diEPP analogs that lack the piperazine ring are also moderately active, providing a demonstration that the diEPP platform may provide an excellent opportunity to flexibly explore chemical space.

Accordingly, one aspect of the disclosure encompasses embodiments of a compound having the formula I, II, III, or IV:

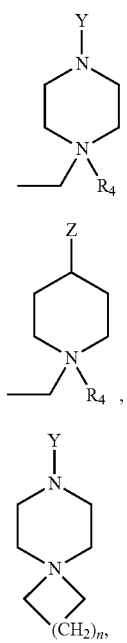

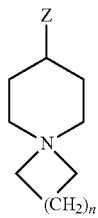

or a pharmaceutically acceptable salt thereof, wherein:

Y can be:

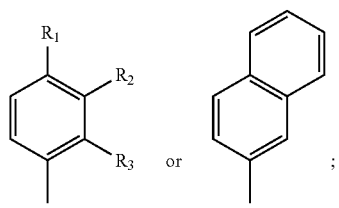

Z can be

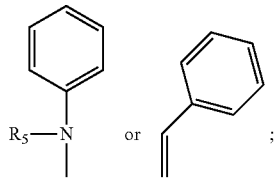

n can be 1, 2, 3, or 4; $R_1$, $R_2$, and $R_3$ can each be independently a hydrogen, an alkyl group, cyano, an alkoxy group, a halogen, a trihaloalkyl, a carboxamide, pentafluorosulfanyl, or hydroxyl, and wherein the halogen is fluorine, chlorine or bromine; $R_4$ can be a hydrogen or an ethyl group; and $R_5$ can be a hydrogen or a carboxytrifluoromethyl.

In some embodiments of this aspect of the disclosure, $R_1$, $R_2$, and $R_3$ can each be independently a hydrogen, a methyl, cyano, methoxy, a halogen, trihaloalkyl, a carboxamide, pentafluorosulfanyl, or hydroxyl.

In some embodiments of this aspect of the disclosure, $R_1$, $R_2$, and $R_3$ can each be independently a hydrogen, a methyl, cyano, methoxy, a halogen, a trihaloalkyl, a carboxamide, pentafluorosulfanyl, or hydroxyl, and $R_5$ is hydrogen.

In some embodiments of this aspect of the disclosure, when $R_1$ is a methyl or a CN, $R_2$ and $R_3$ are each hydrogen; when $R_1$ is a methoxy, $R_2$ is hydrogen $R_3$ is hydrogen or methoxy; when $R_1$ is a halogen, $R_2$ and $R_3$ are each hydrogen; when $R_1$ is a trifluoromethyl, $R_2$ and $R_3$ are each hydrogen; when $R_1$ is a carboxamide, pentafluorosulfanyl, $R_2$ and $R_3$ are each hydrogen; when $R_1$ and $R_3$ are each hydrogen, $R_2$ is a methyl, a CN, a methoxy, a halogen, a trifluoromethyl, or a carboxamide, or OH; when $R_1$ and $R_2$ are each hydrogen, $R_3$ is a methyl or Cl; and $R_4$ is an ethyl group.

Another aspect of the disclosure encompasses embodiments of a pharmaceutical composition comprising a compound having the formula I, II, III, or IV:

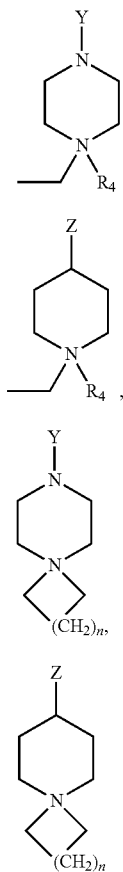

I

II

III

IV or a pharmaceutically acceptable salt thereof, wherein:
Y can be:

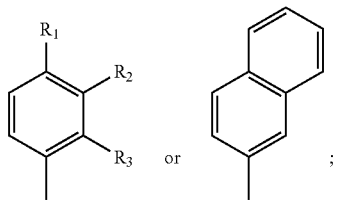

Z can be

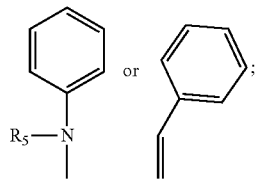

n can be 1, 2, 3, or 4; $R_1$, $R_2$, and $R_3$ can each be independently a hydrogen, an alkyl group, cyano, an alkoxy group, a halogen, a trihaloalkyl, a carboxamide, pentafluorosulfanyl, or hydroxyl, and wherein the halogen is fluorine, chlorine or bromine; $R_4$ can be a hydrogen or an ethyl group; and $R_5$ can be a hydrogen or a carboxytrifluoromethyl; and a pharmaceutically acceptable carrier.

In some embodiments of this aspect of the disclosure, $R_1$, $R_2$, and $R_3$ can each be independently a hydrogen, a methyl, cyano, methoxy, a halogen, trihaloalkyl, a carboxamide, pentafluorosulfanyl, or hydroxyl.

In some embodiments of this aspect of the disclosure, $R_1$, $R_2$, and $R_3$ can each be independently a hydrogen, a methyl, cyano, methoxy, a halogen, a trihaloalkyl, a carboxamide, pentafluorosulfanyl, or hydroxyl, and $R_5$ is hydrogen.

In some embodiments of this aspect of the disclosure, when $R_1$ is a methyl or a CN, $R_2$ and $R_3$ are each hydrogen; when $R_1$ is a methoxy, $R_2$ is hydrogen $R_3$ is hydrogen or methoxy; when $R_1$ is a halogen, $R_2$ and $R_3$ are each hydrogen; when $R_1$ is a trifluoromethyl, $R_2$ and $R_3$ are each hydrogen; when $R_1$ is a carboxamide, pentafluorosulfanyl, $R_2$ and $R_3$ are each hydrogen; when $R_1$ and $R_3$ are each hydrogen, $R_2$ is a methyl, a CN, a methoxy, a halogen, a trifluoromethyl, or a carboxamide, or OH; when $R_1$ and $R_2$ are each hydrogen, $R_3$ is a methyl or Cl; and $R_4$ is an ethyl group.

In some embodiments of this aspect of the disclosure, the composition can be formulated to deliver to a human or animal subject in need thereof, an amount of the compound therapeutically effective in modulating the activity of a nicotinic acetylcholine receptor in the recipient patient, and wherein the therapeutically effective amount can delivered as a single dose or as a series of doses.

In some embodiments of this aspect of the disclosure, the nicotinic acetylcholine receptor positive allosteric modulator (PAM) can be a type II PAM.

In some embodiments of this aspect of the disclosure, the nicotinic acetylcholine receptor positive allosteric modulator (PAM) can be the type II PAM 1-(5-chloro-2,4-dimethoxyphenyl)-3-(5-methylisoxazol-3-yl)urea (PNU-120596).

Yet another aspect of the disclosure encompasses a method of modulating the activity of a nicotinic acetylcholine receptor in an animal or human subject by administering to said subject therapeutically effective doses of a silent agonist of the nicotinic acetylcholine receptor and a nicotinic acetylcholine receptor positive allosteric modulator (PAM).

In some embodiments of this aspect of the disclosure, the silent agonist of the nicotinic acetylcholine receptor and the nicotinic acetylcholine receptor positive allosteric modulator (PAM) can be administered to the subject simultaneously or as consecutive doses.

In some embodiments of this aspect of the disclosure, the silent agonist of the nicotinic acetylcholine receptor is a compound having the formula I, II, III, or IV:

I

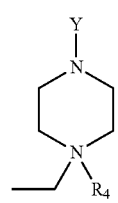

II

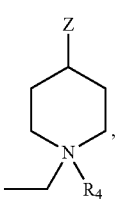

-continued

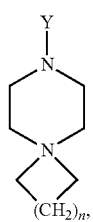
III

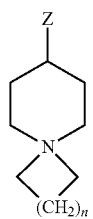
IV or a pharmaceutically acceptable salt thereof, wherein:
Y can be:

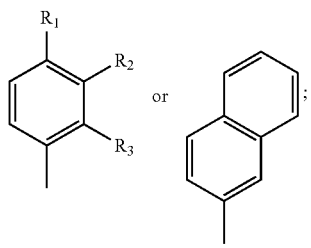

Z can be

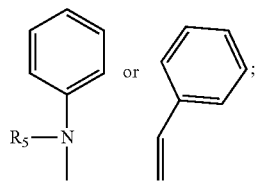

n can be 1, 2, 3, or 4; $R_1$, $R_2$, and $R_3$ can each be independently a hydrogen, an alkyl group, cyano, an alkoxy group, a halogen, a trihaloalkyl, a carboxamide, pentafluorosulfanyl, or hydroxyl, and wherein the halogen is fluorine, chlorine or bromine; $R_4$ is a hydrogen or an ethyl group; and $R_5$ is a hydrogen or a carboxytrifluoromethyl.

In some embodiments of this aspect of the disclosure, the nicotinic acetylcholine receptor positive allosteric modulator (PAM) can be a type II PAM.

In some embodiments of this aspect of the disclosure, the nicotinic acetylcholine receptor positive allosteric modulator (PAM) can be the type II PAM 1-(5-chloro-2,4-dimethoxyphenyl)-3-(5-methylisoxazol-3-yl)urea (PNU-120596).

In some embodiments of this aspect of the disclosure, the composition can be formulated to deliver to a human or animal subject in need thereof, an amount of the compound therapeutically effective in modulating the activity of a nicotinic acetylcholine receptor in the recipient patient, and wherein the therapeutically effective amount is delivered as a single dose or as a series of doses.

It should be emphasized that the embodiments of the present disclosure, particularly any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and protected by the following claims.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified.

EXAMPLES

Example 1

Reagents for chemical synthesis were purchased from Fisher Scientific (Pittsburgh, Pa.), Sigma-Aldrich (St. Louis, Mo.), or Tokyo Chemical Industry (TCI America, Portland, Oreg.). Melting points (uncorrected) were obtained on an MFB-595010M Gallenkamp apparatus equipped with a digital thermometer.

NMR spectra ($^1$H and $^{13}$C) were recorded on a Varian Mercury-300 (300 and 75.0 MHz, respectively) or Varian Inova-500 (5 and 126.0 MHz) instruments using $CDCl_3$, $CD_3OD$, $(CD_3)_2CO$, or $(CD_3)_2SO$ as solvent. Chemical shifts (δ scale) are reported in parts per million (ppm) relative to the peak of the internal standard TMS (δ=0.00 ppm) for $CDCl_3$, $CD_3OD$, $(CD_3)_2CO$ or relative to the central peak of the solvent (δ=2.20 ppm for $(CD_3)_2SO$) in $^1$H NMR and relative to the central peak of the solvent (δ=77.16 ppm for $CDCl_3$, 49.00 for $CD_3OD$, 39.52 for $(CD_3)_2SO$ (DMSO-d6), and 29.84 for $(CD_3)_2CO$ in $^{13}C$ NMR. Processing of the spectra was performed with MestReNova 8.1.1.

Mass spectra were obtained on a Hewlett-Packard 5988A spectrometer or on an Agilent 6220 ESI TOF (Santa Clara, Calif.) mass spectrometer equipped with electrospray and DART sources operated in positive ion mode.

Column chromatography was performed with silica gel (Sigma-Aldrich, 230-4mesh) or neutral alumina. Reactions were monitored by TLC using 0.25 mm silica gel F-254 glass plates (EMD Millipore or neutral alumina TLC plates).

All reagents were of reagent quality or were purified before use. Organic solvents were of analytical grade or were purified by standard procedures. Reactions were carried out in flame-dried glassware and under argon atmosphere when required. In those cases, anhydrous solvents were used in the reactions. Compound purity was >95% as determined by $^1H$ NMR analyses.

Example 2

General Procedure A for the Coupling Reaction of Aryl Halides with 1-Ethylpiperazine to Produce N-Aryl Piperazines 1a-1s:

In a flame-dried and argon-flushed round-bottom flask, a mixture of aryl halide (1 equiv), N-ethylpiperazine (1 equiv), $K_2CO_3$ (2 equiv, for aryl iodide) or $K_3PO_4$ (2 equiv, for aryl bromide), CuI (0 equiv), and L-proline (0.2 equiv) in dry DMSO (1.6 mL/mmol 1-ethylpiperazine) was heated at 90-100° C. until completion (TLC in hexanes/ethyl acetate 9/1).

To the cooled mixture was then added deionized water, the organic layer was separated, and the aqueous layer was extracted three times with ethyl acetate. The combined organic layers were washed with saturated brine, dried over $MgSO_4$, and concentrated in vacuo. The residual oil was purified on a silica gel column eluted with a mixture of ethyl acetate/methanol to afford the corresponding aniline. When coupling aryl bromides, 1-ethylpiperazine and the aryl bromide were used in a 1:1 stoichiometric ratio.

Example 3

1-ethyl-4-p-tolylpiperazine (1a) was obtained by reaction of 4-iodotoluene (114 mg, 0.53 mmol, 1 equiv) and 1-ethylpiperazine (100 μL, 0.79 mmol, 1.5 equiv) (orange oil; 70 mg, 65% yield); $R_f$=0.51 in $CH_2Cl_2$/MeOH 9/1; $^1H$ NMR (CDCl$_3$, 300 MHz): δ 6.99 (d, J=8.2 Hz, 2H), 6.77 (d, J=8.3 Hz, 2H), 3.14-3.06 (m, 4H), 2.59-2.49 (m, 4H), 2.40 (q, J=7.2 Hz, 2H), 2.18 (s, 3H), 1.05 (t, J=7.2 Hz, 3H). $^{13}C$ NMR (CDCl$_3$, 75 MHz) b 149.3, 129. 7, 129.2, 116.5, 53.0, 52.4, 49.7, 20.5, 12.0.

Example 4

4-(4-ethylpiperazin-1-yl)benzonitrile (1b) was obtained by reaction of 4-bromobenzonitrile (191 mg, 1.05 mmol, 1 equiv) and 1-ethylpiperazine (200 μL, 1.mmol, 1.5 equiv) (orange oil; 142 mg, 63% yield); $R_f$=0.48 in $CH_2Cl_2$/MeOH 9/1; $^1H$ NMR (CDCl$_3$, 300 MHz): δ 7.41 (d, J=8.8 Hz, 1H), 6.79 (d, J=9.3 Hz, 1H), 3.31-3.25 (m, 4H), 2.55-2.49 (m, 4H), 2.41 (q, J=7.2 Hz, 2H), 1.06 (t, J=7.2 Hz, 3H). $^{13}C$ NMR (CDCl$_3$, 75 MHz): δ 153.4, 133.5, 120.2, 114.2, 100.2, 52.4, 52.4, 47.2, 12.0. HMRS [M+H]$^+$ ($C_{13}H_{18}N_3$) Calcd 216.1495, Found 216.1499.

Example 5

1-ethyl-4-(4-methoxyphenyl)piperazine (1c) was obtained by reaction of 4-iodoanisole (616 mg, 2.63 mmol, 1 equiv) and 1-ethylpiperazine (500 μL, 3.94 mmol, 1.5 equiv) (pale yellow solid; 302 mg, 52% yield); m.p.=56.6-57.8° C.; $R_f$=0.44 in $CH_2Cl_2$/MeOH 9/1; $^1H$ NMR (CDCl$_3$, 300 MHz): δ 6.84 (d, J=9.1 Hz, 2H), 6.77 (d, J=9.2 Hz, 2H), 3.70 (s, 3H), 3.09-3.02 (m, 4H), 2.60-2.52 (m, 4H), 2.41 (q, J=7.3 Hz, 2H), 1.06 (t, J=7.2 Hz, 3H). $^{13}C$ NMR (CDCl3, 75 MHz): δ 153.7, 145.7, 118.1, 114.4, 55.5, 52.9, 52.3, 50.6, 12.0.

Example 6

1-ethyl-4-m-tolylpiperazine (1d) was obtained by reaction of 3-bromotoluene (320 μL, 450 mg, 2.63 mmol, 1 equiv) and 1-ethylpiperazine (500 μL, 3.94 mmol, 1.5 equiv) (yellow oil; 106 mg, 20% yield); $R_f$=0.51 in $CH_2Cl_2$/MeOH 9/1; $^1H$ NMR (CDCl$_3$, 300 MHz): δ 7.15 (tt, J=8.1, 1.1 Hz, 1H), 6.78-6.74 (m, 2H), 6.74-6.66 (m, 2H), 3.26-3.18 (m, 4H), 2.66-2.59 (m, 4H), 2.49 (q, J=7.2 Hz, 2H), 2.31 (s, 3H), 1.13 (t, J=7.Hz, 3H). $^{13}C$ NMR (CDCl$_3$, 75 MHz): δ 151.5, 138.9, 129.0, 120.7, 117.0, 113.3, 52.9, 52.4, 49.2, 21.9, 12.0.

Example 7

1-(4-chlorophenyl)-4-ethylpiperazine (1e) was obtained by reaction of 4-chlorobromobenzene (504 mg, 2.63 mmol, 1 equiv) and 1-ethylpiperazine (500 μL, 3.94 mmol, 1.5 equiv) (pale orange oil; 146 mg, 25% yield); $R_f$=0.55 in $CH_2Cl_2$/MeOH 9/1; $^1H$ NMR (CDCl$_3$, 300 MHz): δ 7.13 (d, J=9.1 Hz, 1H), 6.77 (d, J=9.0 Hz, 2H), 3.15-3.08 (m, 4H), 2.57-2.51 (m, 4H), 2.41 (q, J=7.2 Hz, 2H), 1.06 (t, J=7.2 Hz, 3H). $^{13}C$ NMR (75 MHz, CDCl$_3$): b 150.1, 129.1, 124.6, 117.3, 52.8, 52.5, 49.3, 12.1. HMRS [M+H]$^+$ ($C_{12}H_{18}ClN_2$) Calcd 225.1153, Found 225.1155.

Example 8

1-(3-chlorophenyl)-4-ethylpiperazine (1f) was obtained by reaction of 1-chloro-3-iodobenzene (1.3 mL, 2.50 g, 10.50 mmol, 1 equiv) and 1-ethylpiperazine (2.0 mL, 15.75 mmol, 1.5 equiv) (orange oil; 1.96 g, 83% yield); $R_f$=0.53 in $CH_2Cl_2$/MeOH 9/1; $^1H$ NMR (CDCl$_3$, 300 MHz): δ 7.15 (t, J=8.1 Hz, 1H), 6.88 (t, J=2.2 Hz, 1H), 6.82-6.75 (m, 2H), 3.25-3.19 (m, 4H), 2.62-2.56 (m, 4H), 2.47 (q, J=7.2 Hz, 2H), 1.13 (t, J=7.2 Hz, 3H). $^{13}C$ NMR (CDCl$_3$, 75 MHz): δ 152.4, 135.0, 130.0, 119.2, 115.7, 113.8, 52.7, 52.4, 48.7, 12.1. HMRS [M$^+$H]$^+$ ($C_{12}H_{18}ClN_2$) Calcd 225.1153, Found 225.1149.

Example 9

1-ethyl-4-(3-methoxyphenyl)piperazine (1g) was obtained by reaction of 3-iodoanisole (1.25 mL, 2.46 g, 10.50 mmol, 1 equiv) and 1-ethylpiperazine (2.0 mL, 15.75 mmol, 1.5 equiv) (red oil, 1.62 g, 70% yield); $R_f$=0.50 in $CH_2Cl_2$/MeOH 9/1; $^1H$ NMR (CDCl$_3$, 300 MHz): δ 7.08 (t, J=8.2 Hz, 1H), 6.46 (ddd, J=8.3, 2.3, 1.0 Hz, 1H), 6.39 (t, J=2.3 Hz, 1H), 6.33 (ddd, J=8.2, 2.3, 0.9 Hz, 1H), 3.70 (s, 3H), 3.17-3.10 (m, 4H), 2.55-2.49 (m, 4H), 2.39 (q, J=7.2 Hz, 1H), 1.05 (t, J=7.2 Hz, 3H). $^{13}C$ NMR (CDCl$_3$, 75 MHz): δ 160.7, 152.8, 129.8, 108.9, 104.4, 102.5, 55.2, 52.91, 52.4, 49.1, 12.1.

Example 10

1-ethyl-4-o-tolylpiperazine (1h) was obtained by reaction of 2-iodotoluene (1.34 mL, 2.29 g, 10.50 mmol, 1 equiv) and 1-ethylpiperazine (2.0 mL, 15.75 mmol, 1.5 equiv) (reddish oil; 386 mg, 18% yield); $R_f$=0.51 in $CH_2Cl_2$/MeOH 9/1; $^1$H NMR (CDCl$_3$, 300 MHz): δ 7.20-7.12 (m, 2H), 7.06-7.01 (m, 1H), 7.00-6.94 (m, 1H), 3.00-2.94 (m, 4H), 2.69-2.57 (m, 4H), 2.51 (q, J=7.3 Hz, 2H), 2.30 (s, 3H), 1.14 (t, J=7.3 Hz, 3H). $^{13}$C NMR (CDCl$_3$, 75 MHz): δ 151.6, 132.6, 131.1, 126.6, 123.2, 119.1, 53.4, 52.5, 51.7, 18.0, 12.1.

Example 11

3-(4-ethylpiperazin-1-yl)benzonitrile (1i) was obtained by reaction of 3-bromobenzonitrile (1.92 g, 10.50 mmol, 1 equiv) and 1-ethylpiperazine (2.0 mL, 15.75 mmol, 1.5 equiv) (pale orange oil; 1.36 g, 60% yield); $R_f$=0.48 in $_{CH2Cl2}$/MeOH 9/1; 1H NMR (CDCl$_3$, 500 MHz): δ 7.35-7.28 (m, 1H), 7.14-7.07 (m, 3H), 3.29-3.22 (m, 4H), 2.65-2.58 (m, 4H), 2.48 (q, J=7.2 Hz, 2H), 1.14 (t, J=7.2 Hz, 3H). $^{13}$C NMR (CDCl$_3$, 126 MHz): δ 151.5, 130.0, 122.5, 119.9, 119.5, 118.5, 113.2, 52.6, 52.4, 48. 5, 12.1.

Example 12

1-(2-chlorophenyl)-4-ethylpiperazine (1j) was obtained by reaction of 1-chloro-2-iodobenzene (2.50 g, 10.50 mmol, 1 equiv) and 1-ethylpiperazine (2.0 mL, 15.75 mmol, 1.5 equiv) (brown oil; 110 mg, 5% yield); $R_f$=0.53 in $CH_2Cl_2$/MeOH 9/1; $^1$H NMR (CDCl$_3$, 300 MHz): δ 7.35 (dd, J=7.9, 1.5 Hz, 1H), 7.22 (td, J=7.3, 1.5 Hz, 1H), 7.06 (dd, J=8.0, 1.6 Hz, 1H), 6.97 (td, J=7.6, 1.5 Hz, 1H), 3.18-3.06 (m, 4H), 2.75-2.62 (m, 4H), 2.53 (q, J=7.2 Hz, 2H), 1.14 (t, J=7.2 Hz, 3H). $^{13}$C NMR (CDCl$_3$, 75 MHz): δ 149.3, 130.7, 128.9, 127.7, 123.8, 120.5, 53.0, 52.4, 51.1, 12.0.

Example 13

3-(4-ethylpiperazin-1-yl)phenol (1k) was obtained by reaction of 3-iodophenol (2.31 g, 10.50 mmol, 1 equiv) and 1-ethylpiperazine (2.0 mL, 15.75 mmol, 1.5 equiv) (brown solid; 703 mg, 32% yield); m.p.=150.3-151.6° C.; $R_f$=0.38 in $CH_2Cl_2$/MeOH 85/15; $^1$H NMR (CD$_3$OD, 300 MHz): δ 7.03 (t, J=8.1 Hz, 1H), 6.45 (ddd, J=8.2, 2.4, 0.9 Hz, 1H), 6.40 (t, J=2.3 Hz, 1H), 6.30 (ddd, J=8.0, 2.3, 0.9 Hz, 1H), 3.20-3.11 (m, 4H), 2.68-2.57 (m, 4H), 2.49 (q, J=7.2 Hz, 2H), 1.14 (t, J=7.2 Hz, 3H). $^{13}$C NMR (CD$_3$OD, 75 MHz): δ 159.2, 154.0, 130.8, 109.0, 108.3, 104.5, 53.7, 53.3, 50.0, 11.8. HMRS [M+H]$^+$ ($C_{12}H_{19}N_2O$) Calcd 207.1492, Found 207.1496.

Example 14

1-(2,4-dimethoxyphenyl)-4-ethylpiperazine (1l) was obtained by reaction of 1-bromo-2,4-dimethoxybenzene (2.28 g, 1.51 mL, 10.5 mmol, 1 equiv) and 1-ethylpiperazine (2.0 mL, 15.75 mmol, 1.5 equiv) (brown oil; 839 mg, 32% yield); $R_f$=0.36 in $CH_2Cl_2$/MeOH 9/1; $^1$H NMR (CDCl$_3$, 300 MHz): δ 6.88 (d, J=8.5 Hz, 1H), 6.48 (d, J=2.6 Hz, 1H), 6.43 (dd, J=8.6, 2.7 Hz, 1H), 3.84 (s, 3H), 3.78 (s, 3H), 3.14-2.97 (m, 4H), 2.75-2.57 (m, 4H), 2.49 (q, J=7.2 Hz, 2H), 1.13 (t, J=7.2 Hz, 3H). $^{13}$C NMR (CDCl$_3$, 75 MHz): δ 156.2, 153.5, 135.4, 118.6, 103.4, 100.0, 55.6, 55.5, 53.3, 52.5, 51.3, 12.1.

Example 15

1-ethyl-4-(naphthalen-2-yl)piperazine (1m) was obtained by reaction of 2-bromonaphthalene (2.17 g, 10.5 mmol, 1 equiv) and 1-ethylpiperazine (2.0 mL, 15.75 mmol, 1.5 equiv) (brownish solid; 1.02 g, 40% yield); m.p.=69.1-70.0° C.; $R_f$=0.38 in $CH_2Cl_2$/MeOH 9/1; $^1$H NMR (CDCl$_3$, 300 MHz): δ 7.76-7.65 (m, 3H), 7.39 (ddd, J=8.1, 6.8, 1.4 Hz, 1H), 7.33-7.24 (m, 2H), 7.12 (d, J=2.5 Hz, 1H), 3.39-3.27 (m, 4H), 2.74-2.62 (m, 4H), 2.60 (s, DMSO), 2.51 (q, J=7.2 Hz, 2H), 1.15 (t, J=7.2 Hz, 3H). $^{13}$C NMR (CDCl$_3$, 75 MHz): δ 149.3, 134.7, 128.8, 128.6, 127.5, 126.8, 126.3, 123.4, 119.4, 110.3, 53.0, 52.5, 49.6, 41.1 (DMSO), 12.2.

Example 16

1-ethyl-4-(4-(trifluoromethyl)phenyl)piperazine (1n) was obtained by reaction of 1-iodo-4-(trifluoromethyl)benzene (2.86 g, 1.54 mL, 10.50 mmol, 1 equiv) and 1-ethylpiperazine (2.0 mL, 15.75 mmol, 1.5 equiv) (white solid; 2.20 g, 81% yield); m.p.=56.3-56.5° C.; $R_f$=0.51 in $CH_2Cl_2$/MeOH 9/1; $^1$H NMR (CDCl$_3$, 300 MHz): δ 7.48 (d, J=8.6 Hz, 2H), 6.92 (d, J=8.6 Hz, 2H), 3.36-3.26 (m, 4H), 2.64-2.56 (m, 4H), 2.48 (q, J=7.2 Hz, 2H), 1.14 (t, J=7.2 Hz, 3H). $^{13}$C NMR (CDCl$_3$, 126 MHz): δ 153.45, 126.44, 125.0 (q, J=276 Hz) 120.4 (q, J=37 Hz), 114.5, 52.7, 52.5, 48.1, 12.1. HMRS [M+H]$^+$ ($C_{13}H_{18}F_3N_2$) Calcd 259.1417, Found 259.1426.

Example 17

1-ethyl-4-(3-(trifluoromethyl)phenyl)piperazine (1o) was obtained by reaction of 3-bromobenzotrifluoride (2.36 g, 1.47 mL, 10.50 mmol, 1 equiv) and 1-ethylpiperazine (2.0 mL, 15.75 mmol, 1.5 equiv) (yellow oil; 1.73 g, 64% yield); $R_f$=0.54 in $CH_2Cl_2$/MeOH 9/1; $^1$H NMR (CDCl$_3$, 300 MHz): δ 7.39-7.29 (m, 1H), 7.14-7.10 (m, 1H), 7.09-7.03 (m, 2H), 3.31-3.21 (m, 4H), 2.66-2.57 (m, 4H), 2.48 (q, J=7.2 Hz, 2H), 1.13 (t, J=7.2 Hz, 3H). $^{13}$C NMR (CDCl$_3$, 126 MHz): δ 151.5, 131.5 (q, J=31 Hz) 129.6, 124.4, (q, J=271 Hz) 118.6, 115.7, 112.1, 52.7, 52.4, 48.7, 12.1. HMRS [M+H]$^+$ ($C_{13}H_{18}F_3N_2$) Calcd 259.1417, Found 259.1423.

Example 18

1-(3-bromophenyl)-4-ethylpiperazine (1p) was obtained by reaction of 1,3-dibromobenzene (3.72 g, 1.90 mL, 15.75 mmol, 1 equiv) and 1-ethylpiperazine (2.0 mL, 15.75 mmol, 1.5 equiv) (reddish oil, 1.60 g, 38% yield); $R_f$=0.49 in $CH_2Cl_2$/MeOH 9/1; $^1$H NMR (CDCl$_3$, 300 MHz): δ 7.09 (t, J=8.1 Hz, 1H), 7.05-7.01 (m, 1H), 6.97-6.91 (m, 1H), 6.86-6.79 (m, 1H), 3.26-3.16 (m, 4H), 2.63-2.53 (m, 4H), 2.46 (q, J=7.2 Hz, 2H), 1.12 (t, J=7.2 Hz, 3H). $^{13}$C NMR (CDCl$_3$, 75 MHz): δ 152.5, 130.3, 123.3, 122.1, 118.6, 114.3, 52.7, 52.4, 48.7, 12.1. HMRS [M+H]$^+$ ($C_{12}H_{18}BrN_2$) Calcd 269.0648, Found 269.0641.

Example 19

1-(4-bromophenyl)-4-ethylpiperazine (1q) was obtained by reaction of 1,4-dibromobenzene (2.48 g, 10.50 mmol, 1 equiv) and 1-ethylpiperazine (1.33 mL, 10.50 mmol, 1.5 equiv) (off-white solid; 913 mg, 32% yield); m.p.=85.0-85.5° C.; $R_f$=0.49 in $CH_2Cl_2$/MeOH 9/1; $^1$H NMR (CDCl$_3$, 300 MHz): δ 7.33 (d, J=9.0 Hz, 2H), 6.79 (d, J=9.0 Hz, 2H), 3.24-3.13 (m, 4H), 2.65-2.55 (m, 4H), 2.47 (q, J=7.2 Hz, 2H), 1.13 (t, J=7.2 Hz, 3H). $^{13}$C NMR (CDCl$_3$, 75 MHz): δ 150.4, 131.9, 117.6, 111.8, 52.8, 52.4, 49.1, 12.1.

Example 20

1-ethyl-4-(4-fluorophenyl)piperazine (1r) was obtained by reaction of 4-fluoroiodobenzene (2.33 g, 1.21 mL, 10.50 mmol, 1 equiv) and 1-ethylpiperazine (2.0 mL, 15.75 mmol, 1.5 equiv) (yellowish solid; 1.77 g, 81% yield); m.p.=30.0-30.5° C.; $R_f$=0.46 in $CH_2Cl_2$/MeOH 9/1; $^1$H NMR ($CDCl_3$, 300 MHz): δ 7.02-6.92 (m, 2H), 6.92-6.84 (m, 2H), 3.20-3.10 (m, 4H), 2.66-2.57 (m, 4H), 2.48 (q, J=7.3 Hz, 2H), 1.13 (t, J=7.2 Hz, 3H). $^{13}$C NMR ($CDCl_3$, 75 MHz): δ 157.2 (d, J=239 Hz), 148.1, 117. 8 (d, J=8 Hz) 115.5 (d, J=22 Hz), 52.9, 52.4, 50.2, 12.1.

Example 21

1-ethyl-4-(3-fluorophenyl)piperazine (1s) was obtained by reaction of 3-fluoroiodobenzene (2.33 g, 1.23 mL, 10.50 mmol, 1 equiv) and 1-ethylpiperazine (2.0 mL, 15.75 mmol, 1.5 equiv) (yellow oil; 697 mg, 75% yield); $R_f$=0.49 in $CH_2Cl_2$/MeOH 9/1; $^1$H NMR ($CDCl_3$, 300 MHz): δ 7.23-7.12 (m, 1H), 6.71-6.64 (m, 1H), 6.63-6.55 (m, 1H), 6.55-6.47 (m, 1H), 3.27-3.17 (m, 4H), 2.64-2.54 (m, 4H), 2.47 (q, J=7.2 Hz, 2H), 1.13 (t, J=7.2 Hz, 3H). $^{13}$C NMR (75 MHz, $CDCl_3$): b 164.0 (d, J=243 Hz), 153.1 (d, J=10 Hz), 130.2 (d, J=10 Hz), 111.1 (d, J=2 Hz), 105.8 (d, J=22 Hz), 102.7 (d, J=25 Hz), 52.8, 52.5, 48.7, 12.1.

Example 22

General Procedure B for Ethylation to Quaternary Ammonium Salts 2a-2s:

In a sealed vial, the coupled compound (1 equiv) was dissolved in dry THF; after addition of some copper as stabilizer, iodoethane (7 equiv) was added, and the resulting mixture was heated at 90° C. until complete consumption of the starting material (TLC in methylene chloride/methanol 9/1). Upon completion, the mixture was cooled to room temperature and the solvent removed in vacuo. The crude was then purified by crystallization, directly or after a chromatography (silica column, elution in methylene chloride/methanol 9:1. Except as noted, all quaternary ammonium derivatives were crystallized from a mixture of hot THF and ethanol, with addition of a few drops of hexanes.

Example 23

1,1-diethyl-4-p-tolylpiperazin-1-ium iodide (2a). Obtained from 1-ethyl-4-ptolylpiperazine, 1a (50 mg, 0.25 mmol, 1 equiv) and EtI (141 μL), followed by crystallization in 2-propanol. Yellow solid (60 mg, 68% yield); m.p.=147.4-148.8° C.; $R_f$=0.37 in $CH_2Cl_2$/MeOH 8/2; $^1$H NMR (DMSO-d6, 300 MHz): δ 7.09 (d, J=8.3 Hz, 2H), 6.91 (d, J=8.4 Hz, 2H), 3.58-3.50 (m, 4H), 3.51-3.37 (m, 8H), 2.22 (s, 3H), 1.21 (t, J=7.2 Hz, 6H). $^{13}$C NMR (DMSO-d6, 75 MHz): δ 147.2, 129.5, 128.8, 115.8, 56.5, 51.9, 42.0, 20.1, 6.7. HMRS [M]$^+$ ($C_{15}H_{25}N_2^+$) Calcd 233.2012, Found 233.2017.

Example 24

4-(4-cyanophenyl)-1,1-diethylpiperazin-1-ium iodide (2b). Obtained from 4-(4-ethylpiperazin-1-yl)benzonitrile (142 mg, 0.66 mmol, 1 equiv) and EtI (371 μL), followed by silica column and crystallization. Light yellow crystals (35 mg, 14% yield); m.p.=197.4-198.2° C.; $R_f$=0.31 in $CH_2Cl_2$/MeOH 8/2; $^1$H NMR ($CD_3OD$, 300 MHz): δ 7.59 (d, J=8.9 Hz, 1H), 7.13 (d, J=8.9 Hz, 2H), 3.80-3.71 (m, 4H), 3.71-3.65 (m, 4H), 3.60 (q, J=7.3 Hz, 4H), 1.38 (t, J=7.3 Hz, 6H). $^{13}$C NMR ($CD_3OD$, 300 MHz): δ 153.6, 134.6, 120.6, 116.2, 102.5, 58.2, 54.3, 42.1, 7.6. HMRS [M]$^+$ ($C_{15}H_{22}N_3^+$) Calcd 244.1808, Found 244.1813.

Example 25

1,1-diethyl-4-(4-methoxyphenyl)piperazin-1-ium iodide (2c). Obtained from 1-ethyl-4-(4-methoxyphenyl)piperazine 1c, (270 mg, 1.23 mmol, 1 equiv) and EtI (692 μL), followed by crystallization. Bright yellowish crystal (334 mg, 72% yield); m.p.=150.5-153.1° C.; $R_f$=0.35 in $CH_2Cl_2$/MeOH 8/2; $^1$H NMR ($CD_3OD$, 500 MHz): δ 7.01 (d, J=9.1 Hz, 2H), 6.88 (d, J=9.1 Hz, 2H), 3.75 (s, 3H), 3.65-3.59 (m, 4H), 3.54 (q, J=7.3 Hz, 4H), 3.45-3.39 (m, 4H), 1.36 (t, J=7.3 Hz, 6H). $^{13}$C NMR ($CD_3OD$, 126 MHz): δ 156.4, 145.0, 119.9, 115.6, 59.0, 56.0, 54.3, 45.4, 7.4. HMRS [M]$^+$ ($C_{15}H_{25}N_2O^+$) Calcd 249.1961 Found 249.1972.

Example 26

1,1-diethyl-4-m-tolylpiperazin-1-ium iodide (2d). Obtained from 1-ethyl-4-mtolylpiperazine 1d, (101 mg, 0.49 mmol, 1 equiv) and EtI (276 μL), followed by crystallization. Yellow crystals (77 mg, 43% yield); m.p.=144.0-145.0° C.; $R_f$=0.37 in $CH_2Cl_2$/MeOH 8/2; $^1$H NMR ($CD_3OD$, 500 MHz): δ 7.16 (t, J=7.9 Hz, 1H), 6.88-6.85 (m, 1H), 6.82 (dd, 1H), 6.78-6.74 (m, 1H), 3.64-3.59 (m, 4H), 3.56-3.48 (m, 8H), 2.31 (s, 3H), 1.40-1.33 (m, 6H). $^{13}$C NMR ($CD_3OD$, 126 MHz): δ 150.9, 140.2, 130.1, 123.0, 118.3, 114.7, 58.8, 54.2, 44.1, 21.7, 7.4. HMRS [M]$^+$ ($C_{15}H_{25}N_2^+$) Calcd 233.2012 Found 233.2023.

Example 27

4-(4-chlorophenyl)-1,1-diethylpiperazin-1-ium iodide (2e). Obtained from 1-(4-chlorophenyl)-4-ethylpiperazine 1e (146 mg, 0.65 mmol, 1 equiv) and EtI (366 μL), followed by crystallization. Yellowish solid (126 mg, 51% yield); m.p.=151.0-152.1° C.; $R_f$=0.33 in $CH_2Cl_2$/MeOH 8/2; $^1$H NMR ($CD_3OD$, 500 MHz): δ 7.27 (d, J=9.1 Hz, 2H), 7.01 (d, J=9.0 Hz, 2H), 3.65-3.60 (m, 4H), 3.57-3.50 (m, 8H), 1.36 (t, J=7.2 Hz, 6H). $^{13}$C NMR ($CD_3OD$, 126 MHz): δ 149.6, 130.1, 127.0, 118.9, 58.6, 54.3, 43.8, 7.4. HMRS [M]$^+$ ($C_{14}H_{22}ClN_2^+$) Calcd 253.1466, Found 253.1476 [M], 255.1449 [M+2].

Example 28

4-(3-chlorophenyl)-1,1-diethylpiperazin-1-ium iodide (2f). Obtained from 1-(3-chlorophenyl)-4-ethylpiperazine 1f (501 mg, 2.23 mmol, 1 equiv) and EtI (1.25 mL), followed by crystallization. White crystals (412 mg, 48% yield); m.p.=155.0-156.3° C.; $R_f$=0.33 in $CH_2Cl_2$/MeOH 8/2; $^1$H NMR ($CD_3OD$, 300 MHz): δ 7.26 (d, J=8.4 Hz, 1H), 7.05 (t, J=2.2 Hz, 1H), 6.96 (ddd, J=8.4, 2.5, 0.9 Hz, 1H), 6.90 (ddd, J=7.9, 1.9, 0.8 Hz, 1H), 3.66-3.60 (m, 4H), 3.55 (q, J=7.2 Hz, 4H), 3.60-3.53 (m, 4H), 1.37 (t, J=7.2 Hz, 6H). $^{13}$C NMR ($CD_3OD$, 126 MHz): δ 152.1, 136.1, 131.5, 121.6, 117.2, 115.6, 58.5, 54.3, 43.5, 7.4. HMRS [M]$^+$ ($C_{14}H_{22}ClN_2^+$) Calcd 253.1466, Found 253.1475 [M], 255.1443 [M+2].

Example 29

1,1-diethyl-4-(3-methoxyphenyl)piperazin-1-ium iodide (2g). Obtained from 1-ethyl-4-(3-methoxyphenyl)piperazine 1g (503 mg, 2.28 mmol, 1 equiv) and EtI (1.28 mL), followed by crystallization. White crystals (649 mg, 76% yield); m.p.=146.0-147.0° C.; $R_f$=0.35 in $CH_2Cl_2$/MeOH 8/2; $^1$H NMR ($CD_3OD$, 500 MHz): δ 7.19 (t, J=8.2 Hz, 1H), 6.62 (dt, J=8.2, 1.4 Hz, 1H), 6.57 (t, J=2.4 Hz, 1H), 6.51 (dd, J=8.2, 2.3 Hz, 1H), 3.77 (s, 3H), 3.64-3.60 (m, 4H), 3.54 (q, J=7.1 Hz, 4H), 3.54-3.50 (m, 4H), 1.36 (t, J=7.4 Hz, 6H). 13C NMR (CD$_3$OD, 126 MHz): δ 162.2, 152.2, 131.1, 110.1, 107.3, 104.0, 58.7, 55.8, 54.3, 44.0, 7.4. HMRS [M]$^+$ (C$_{15}$H$_{25}$N$_2$O$^+$) Calcd 249.1961, Found 249.1966.

Example 30

1,1-diethyl-4-o-tolylpiperazin-1-ium iodide (2h). Obtained from 1-ethyl-4-o-tolylpiperazine 1h, (385 mg, 1.88 mmol, 1 equiv) and EtI (1.06 mL), followed by crystallization in THF/ethanol/MeOH. Bright white crystals (301 mg, 45% yield); m.p.=158.5-160.2° C.; R$_f$=0.37 in CH$_2$Cl$_2$/MeOH 8/2; $^1$H NMR (CD$_3$OD, 500 MHz): δ 7.26-7.16 (m, 3H), 7.07-7.01 (m, 1H), 3.67-3.62 (m, 4H), 3.60 (q, J=7.4 Hz, 4H), 3.29-3.23 (m, 4H), 2.33 (s, 3H), 1.38 (t, J=7.1 Hz, 6H). $^{13}$C NMR (CD$_3$OD, 126 MHz): δ 147.2, 129.5, 128.8, 115.8, 56.5, 51.9, 42.0, 20.1, 6.7. HMRS [M]$^+$ (C$_{15}$H$_{25}$N$_2$$^+$) Calcd 233.2012 Found 233.2023.

Example 31

4-(3-cyanophenyl)-1,1-diethylpiperazin-1-ium iodide (2i). Obtained from 3-(4-ethylpiperazin-1-yl)benzonitrile 1i, (555 mg, 2.58 mmol, 1 equiv) and EtI (1.45 mL), followed by crystallization from THF/ethanol/MeOH. Colorless crystals (140 mg, 15% yield); m.p.=210-212° C.; R$_f$=0.31 in CH$_2$Cl$_2$/MeOH 8/2; $^1$H NMR (CD$_3$OD, 300 MHz): δ 7.50-7.40 (m, 1H), 7.40-7.32 (m, 2H), 7.22 (dt, J=7.4, 1.3 Hz, 1H), 3.71-3.62 (m, 8H), 3.58 (q, J=7.3 Hz, 4H), 1.38 (t, J=8.2 Hz, 6H). $^{13}$C NMR (CD$_3$OD, 75 MHz): δ 151.3, 131.5, 124.9, 121.7, 119.9, 119.9, 114.2, 58.4, 54.2, 43.1, 7.4. HMRS [M]$^+$ (C$_{15}$H$_{25}$N$_2$$^+$) Calcd 244.1808 Found 244.1812.

Example 32

4-(2-chlorophenyl)-1,1-diethylpiperazin-1-ium iodide (2j). Obtained from 1-(2-chlorophenyl)-4-ethylpiperazine 1j, (110 mg, 0.49 mmol, 1 equiv) and EtI (276 μL), followed by crystallization. White crystals (40 mg, 21% yield); m.p.=154.1-156.8° C.; R$_f$=0.33 in CH$_2$Cl$_2$/MeOH 8/2; $^1$H NMR (CD$_3$OD, 300 MHz): δ 7.47-7.39 (m, 1H), 7.37-7.28 (m, 2H), 7.17-7.06 (m, 1H), 3.72-3.55 (m, 8H), 3.49-3.39 (m, 4H), 1.38 (t, J=7.2 Hz, 5H). $^{13}$C NMR (CD$_3$OD, 75 MHz): δ 148.4, 131.7, 130.0, 129.2, 126.5, 122.4, 59.3, 54.5, 45.7, 7.4. HMRS [M]$^+$ (C$_{14}$H$_{22}$ClN$_2$$^+$) Calcd 253.1472, Found 253.1483 [M], 255.1437 [M+2].

Example 33

1,1-diethyl-4-(3-hydroxyphenyl)piperazin-1-ium iodide (2k). Obtained from 3-(4-ethylpiperazin-1-yl)phenol 1k, (489 mg, 2.37 mmol, 1 equiv) and EtI (1.33 mL), followed by crystallization from ethanol. Off-white solid (186 mg, 22% yield); m.p.=200-203° C.; R$_f$=0.38 in CH$_2$Cl$_2$/MeOH 75/25; $^1$H NMR (DMSO-d6, 300 MHz): δ 9.26 (s, 1H), 7.04 (t, J=8.1 Hz, 1H), 6.48-6.41 (m, 1H), 6.38-6.34 (m, 1H), 6.33-6.27 (m, 1H), 3.58-3.38 (m, 12H), 1.21 (t, J=7.1 Hz, 6H). $^{13}$C NMR (DMSO-d6, 75 MHz): δ 158.1, 150.7, 129.7, 107.1, 106.6, 102.6, 56.4, 51.9, 41.5, 6.8. HMRS [M]$^+$ (C$_{14}$H$_{23}$N$_2$O$^+$) Calcd 235.1805 Found 235.1806.

Example 34

4-(2,4-dimethoxyphenyl)-1,1-diethylpiperazin-1-ium iodide (2l). Obtained from 1-(2,4-dimethoxyphenyl)-4-ethylpiperazine 1l, (502 mg, 2.01 mmol, 1 equiv) and EtI (1.13 mL), followed by crystallization. White solid (236 mg, 29% yield); m.p.=187.0-188.8° C.; R$_f$=0.34 in CH$_2$Cl$_2$/MeOH 8/2; $^1$H NMR (CD$_3$OD, 300 MHz): δ 7.01 (d, J=8.6 Hz, 1H), 6.57 (d, J=2.7 Hz, 1H), 6.49 (dd, J=8.6, 2.7 Hz, 1H), 3.84 (s, 3H), 3.76 (s, 3H), 3.63-3.49 (m, 8H), 3.36-3.28 (m, 4H), 1.36 (t, J=7.3 Hz, 6H). $^{13}$C NMR (CD$_3$OD, 75 MHz): δ 158.8, 155.2, 133.8, 121.5, 105.3, 100.9, 59.3, 56.2, 56.0, 54.5, 45.6, 7.5. HMRS [M]$^+$ (C$_{16}$H$_{27}$N$_2$O$_2$$^+$) Calcd 279.2067 Found 279.2078.

Example 35

1,1-diethyl-4-(naphthalen-2-yl)piperazin-1-ium iodide (2m). Obtained from 1-ethyl-4-(naphthalen-2-yl)piperazine 1m, (516 mg, 2.15 mmol, 1 equiv) and EtI (1.21 mL), followed by crystallization. Yellowish solid (430 mg, 51% yield); m.p.=218-219° C.; R$_f$=0.38 in CH$_2$Cl$_2$/MeOH 75/25; $^1$H NMR (DMSO-d6, 300 MHz): δ 7.86-7.81 (m, 1H), 7.81-7.73 (m, 2H), 7.43 (ddd, J=8.1, 5.4, 1.9 Hz, 2H), 7.35-7.26 (m, 2H), 3.66-3.58 (m, 8H), 3.52 (q, J=7.1 Hz, 4H), 1.25 (t, J=7.2 Hz, 6H). $^{13}$C NMR (DMSO-d6, 75 MHz): δ 147.1, 134.0, 128.6, 128.1, 127.3, 126.6, 126.4, 123.5, 118.5, 109.8, 56.4, 52.0, 41.8, 6.8. HMRS [M]$^+$ (C$_{18}$H$_{25}$N$_2$$^+$) Calcd 269.2018. Found 269.2013.

Example 36

1,1-diethyl-4-(4-(trifluoromethyl)phenyl)piperazin-1-ium iodide (2n). Obtained from 1-ethyl-4-(4-(trifluoromethyl)phenyl)piperazine 1n, (714 mg, 2.76 mmol, 1 equiv) and EtI (1.60 mL), afforded 546 mg (48% crude) of a yellow solid that was crystallized from methanol. White crystals (70 mg, 6% yield); m.p.=175.2-175.5° C. R$_f$=0.48 in CH$_2$Cl$_2$/MeOH 75/25; $^1$H NMR (DMSO-d6, 300 MHz): δ 7.59 (d, J=8.5 Hz, 2H), 7.15 (d, J=8.6 Hz, 2H), 3.68-3.59 (m, 4H), 3.59-3.53 (m, 4H), 3.48 (q, J=7.2 Hz, 4H), 1.23 (t, J=7.2 Hz, 6H). $^{13}$C NMR (DMSO-d6, 75 MHz): δ 151.9, 124.8 (q, J=271 Hz), 126.2 (q, J=4 Hz), 119.0 (q, J=32 Hz), 114.6, 56.1, 51.9, 40.5, 6.8. HMRS [M]$^+$ (C$_{15}$H$_{22}$F$_3$N$_2$$^+$) Calcd 287.1730. Found 287.1723. Comparison with the $^1$H NMR spectrum prior to recrystallization revealed the crude product was at least 95% pure.

Example 37

1,1-diethyl-4-(3-(trifluoromethyl)phenyl)piperazin-1-ium iodide (2o). Obtained from 1-ethyl-4-(3-(trifluoromethyl)phenyl)piperazine 1o, (701 mg, 2.71 mmol, 1 equiv) and EtI (1.53 mL), followed by crystallization from methanol. (235 mg, 21% yield); NMR analysis indicated approximately 5 mol equivalents of methanol in the crystals, m.p.=207-208° C.; R$_f$=0.48 in CH$_2$Cl$_2$/MeOH 75/25; $^1$H NMR (CD$_3$OD, 300 MHz): δ 7.52-7.43 (m, 1H), 7.32-7.26 (m, 2H), 7.23-7.16 (m, 1H), 3.70-3.61 (m, 8H), 3.56 (q, J=7.3 Hz, 4H), 3.34 (s, methanol), 1.44-1.32 (m, 6H). $^{13}$C NMR (CD$_3$OD, 75 MHz): 151.3, 132.5 (q, J=32 Hz), 131.2, 125.7 (q, J=273 Hz), 120.7, 118.0, 113.5, 58.5, 54.3, 43.4, 7.5. HMRS [M]$^+$ (C$_{15}$H$_{22}$F$_3$N$_2$$^+$) Calcd 287.1730 Found 287.1738.

Example 38

4-(3-bromophenyl)-1,1-diethylpiperazin-1-ium iodide (2p). Obtained from 1-(3-bromophenyl)-4-ethylpiperazine 1p, (768 mg, 2.85 mmol, 1 equiv) and EtI (1.60 mL), followed by crystallization. Brownish white-off crystals (403 mg, 33% yield); m.p.=198.8-199.5° C.; R$_f$=0.37 in CH$_2$Cl$_2$/MeOH 75/25; $^1$H NMR (CD$_3$OD, 300 MHz): δ 7.23-7.16 (m, 2H), 7.08-6.98 (m, 2H), 3.67-3.50 (m, 12H), 1.37 (t, J=7.2 Hz, 6H). $^{13}$C NMR (CD$_3$OD, 75 MHz) δ 152.3, 131.8, 124.6, 124.1, 120.1, 116.0, 58.5, 54.2, 43.5, 7.5. HMRS [M]+(C$_{14}$H$_{22}$BrN$_2$$^+$) Calcd 297.0966 Found 297.0963 [M], 299.0944 [M+2].

Example 39

4-(4-bromophenyl)-1,1-diethylpiperazin-1-ium iodide (2q). Obtained from 1-(4-bromophenyl)-4-ethylpiperazine 1q, (517 mg, 1.92 mmol, 1 equiv) and EtI (1.08 mL), followed by crystallization. White crystals (220 mg, 27% yield); m.p.=182.5-183.6° C.; R$_f$=0.37 in CH$_2$Cl$_2$/MeOH 75/25; $^1$H NMR (CD$_3$OD, 300 MHz): δ 7.40 (d, J=9.0 Hz, 1H), 6.97 (d, J=9.0 Hz, 2H), 3.67-3.48 (m, 12H), 1.42-1.32 (m, 6H). $^{13}$C NMR (CD$_3$OD, 75 MHz): δ 150.0, 133.1, 119.2, 114.1, 58.5, 54.16, 43.7, 7.3. HMRS [M]$^+$ (C$_{14}$H$_{22}$BrN$_2$$^+$) Calcd 297.0961 Found 297.0965 [M], 299.0945 [M+2].

Example 40

1,1-diethyl-4-(4-fluorophenyl)piperazin-1-ium iodide (2r). Obtained from 1-ethyl-4-(4-fluorophenyl)piperazine 1r, (704 mg, 3.38 mmol, 1 equiv) and EtI (1.90 mL), followed by crystallization. White crystals (478 mg, 39% yield); m.p.=194.0-194.3° C.; R$_f$=0.31 in CH$_2$Cl$_2$/MeOH 8/2; $^1$H NMR (CD$_3$OD, 300 MHz): δ 7.08-7.04 (m, 2H), 7.04-7.01 (m, 2H), 3.66-3.59 (m, 4H), 3.58-3.50 (m, 4H), 3.50-3.43 (m, 4H), 1.43-1.30 (m, 6H). $^{13}$C NMR (CD$_3$OD, 75 MHz): δ 159.2 (d, J=240 Hz), 147.6, 119.7 (d, J=8 Hz), 116.6 (d, J=23 Hz), 58.8, 54.3, 44.8, 7.5. HMRS [M]$^+$ (C$_{14}$H$_{22}$FN$_2$$^+$) Calcd 237.1762 Found 237.1767.

Example 41

1,1-diethyl-4-(3-fluorophenyl)piperazin-1-ium iodide (2s). Obtained from 1-ethyl-4-(3-fluorophenyl)piperazine 1s, (801 mg, 3.85 mmol, 1 equiv) and EtI (2.17 mL), followed by purification via chromatography, crystals were not obtained. Off-white solid (901 mg, 64% yield), m.p.=125.0-127.0° C.; R$_f$=0.33 in CH$_2$Cl$_2$/MeOH 8/2; $^1$H NMR (DMSOd6, 300 MHz): δ 7.35-7.23 (m, 1H), 6.92-6.80 (m, 2H), 6.71-6.61 (m, 1H), 3.62-3.51 (m, 8H), 3.48 (q, J=7.6 Hz, 4H), 1.22 (t, J=7.2 Hz, 6H). $^{13}$C NMR (DMSO-d6, 75 MHz): δ 163.1 (d, J=241 Hz), 151.1 (d, J=10 Hz), 130.5 (d, J=10 Hz), 111.0 (d, J=2 Hz), 105.7 (d, J=21 Hz), 102.1 (d, J=25 Hz), 56.1, 51.8, 41.1, 6.8. HMRS [M]$^+$ (C$_{14}$H$_{22}$FN$_2$$^+$) Calcd 237.1762 Found 237.1760.

Example 42

General Procedure for Hydration of Nitrile to Amide with Acetaldoxime:

In an oven-dried, sealed vial under argon atmosphere, a mixture of benzonitrile derivative (2 equiv), acetaldoxime (4 equiv) and Pd(PPh$_3$)$_4$ (0.1 equiv) in EtOH was heated to reflux until complete consumption of the starting material (TLC on neutral alumina CH$_2$Cl$_2$/MeOH 95/5 or 85/15). Upon completion, the reaction mixture was cooled to room temperature, filtered through a Celite pad and washed with hot EtOH. After removal of solvent, the crude was purified with neutral alumina chromatography (CH$_2$Cl$_2$/MeOH 95/5 to 85/15) and the pooled fractions were then crystallized from methanol or ethanol.

Example 43

4-(4-carbamoylphenyl)-1,1-diethylpiperazin-1-ium iodide (2t). Obtained from 4-(4-cyanophenyl)-1,1-diethylpiperazin-1-ium iodide 2b (230 mg, 0.62 mmol, 1 equiv) and acetaldoxime (73 mg, 1.24 mmol, 2 equiv), followed by crystallization from ethanol. White solids (18 mg, 7% yield); m.p.=238-239° C.; R$_f$=0.42 in CH$_2$Cl$_2$/MeOH 8/2 (alumina neutral); $^1$H NMR (CD$_3$OD, 300 MHz): δ 7.84 (d, J=8.8 Hz, 2H), 7.07 (d, J=8.9 Hz, 2H), 3.71-3.60 (m, 8H), 3.55 (q, J=7.3 Hz, 4H), 1.37 (t, J=7.3 Hz, 6H). $^{13}$C NMR (CD$_3$OD, 75 MHz): δ 171.9, 153.4, 130.3, 125.8, 115.7, 58.3, 54.1, 42.6, 7.3. HMRS [M]$^+$ (C$_{15}$H$_{24}$N$_3$O$^+$) Calcd 262.1914 Found 262.1923.

Example 44

4-(3-carbamoylphenyl)-1,1-diethylpiperazin-1-ium iodide (2u). Obtained from 4-(3-cyanophenyl)-1,1-diethylpiperazin-1-ium iodide 2i (273 mg, 0.74 mmol, 1 equiv) and acetaldoxime (87 mg, 1.48 mmol, 2 equiv), followed by crystallization from methanol. Yellow crystals (77 mg, 27% yield) m.p.=212-213° C.; R$_f$=0.42 in CH$_2$Cl$_2$/MeOH 8/2 (neutral alumina); $^1$H NMR (CD$_3$OD, 300 MHz): δ 7.54-7.51 (m, 1H), 7.45-7.35 (m, 2H), 7.26-7.21 (m, 1H), 3.68-3.59 (m, 8H), 3.56 (q, J=7.2 Hz, 4H), 3.34 (s, methanol), 1.37 (t, J=7.3 Hz, 6H). $^{13}$C NMR (CD$_3$OD, 75 MHz): δ 172.3, 151.0, 135.9, 130.5, 120.9, 120.8, 116.4, 58.6, 54.2, 43.7, 7.4. HMRS [M]$^+$ (C$_{15}$H$_{24}$N$_3$O+) Calcd 262.1914 Found 262.1905.

Example 45

1-ethyl-N-phenylpiperidin-4-amine (3). Reductive amination with NaBH$_3$CN. In a flame-dried and argon-flushed round-bottom flask, aniline (1.41 mL, 1.44 g, 15.47 mmol, 1 equiv) was dissolved in dry methanol (freshly distilled from Na), and 1-ethyl-4-piperidone (2.5 mL, 2.36 mg, 18.56 mmol, 1.2 equiv) was added, followed by sodium cyanoborohydride (1.17 g, 18.56 mmol, 1.2 equiv). The pH was adjusted to 6.0 (pH strips) with glacial acetic acid and the mixture stirred at room temperature. (TLC in CH$_2$Cl$_2$/MeOH 95/5). Even after stirring for seven days and heating at reflux, the reaction did not come to completion. Saturated aqueous NaHCO$_3$ was added to quench the reaction, and methanol was removed by rotary evaporation. The residue was partitioned between ethyl acetate and water, and extracted with EtOAc three times. The combined organic layers were dried over MgSO$_4$, and concentrated in vacuo. The residue was chromatographed on silica gel, eluting in CH$_2$Cl$_2$/MeOH 93/7 to give the desired product as an off-white solid (1.88 g, 59%). m.p.=43.0-44.6° C.; R$_f$=0.33 in CH$_2$Cl$_2$/MeOH 75/25; $^1$H NMR (CD$_3$OD, 300 MHz): δ 7.13-7.06 (m, 2H), 6.68-6.57 (m, 3H), 3.41-3.32 (m, 1H), 3.11-3.00 (m, 2H), 2.59 (q, J=7.3 Hz, 2H), 2.39-2.26 (m, 2H), 2.12-2.01 (m, 2H), 1.60-1.45 (m, 2H), 1.15 (t, J=7.3 Hz, 3H). $^{13}$C NMR (CD$_3$OD, 75 MHz): δ 148.9, 130.1, 118.2, 114.8, 53.2, 52.9, 50.6, 32.4, 11.7. HMRS [M+H]$^+$ (C$_{13}$H$_{21}$N$^+$) Calcd 205.1699 Found 205.1701.

Example 46

N-(1-ethylpiperidin-4-yl)-2,2,2-trifluoro-N-phenylacetamide (4). In a flame-dried and argon-flushed round-bottom flask, a solution of 1-ethyl-N-phenylpiperidin-4-amine (3) (1.53 g, 7.46 mmol, 1 equiv) in dry CH$_2$Cl$_2$ (75 mL) was cooled to 0° C. Triethylamine (4.20 mL, 3.02 g, 29.9 mmol, 4 equiv) was added, followed by addition dropwise of the trifluoroacetic anhydride (3.20 mL, 4.70 g, 22.4 mmol, 3 equiv). The resulting mixture was then stirred at 0° C. until completion (5 h) (TLC in CH$_2$Cl$_2$/MeOH 95/5). Deionized water was then added at 0° C., the organic fraction washed with saturated brine, dried over MgSO$_4$, and concentrated in vacuo. The crude obtained was purified by a silica gel column eluting with CH$_2$Cl$_2$/MeOH 95/5 to 9/1, and then the isolated fraction was further purified on a silica gel column eluting in EtOAc/MeOH 100/0 to 9/1 affording the desired product as a yellow solid, (911 mg, 41%); m.p.=50.2-51.3° C.; R$_f$=0.5 in CH$_2$Cl$_2$/MeOH 9/1; $^1$H NMR (CDCl$_3$, 300 MHz): δ 7.45-7.34 (m, 3H), 7.19-7.10 (m, 2H), 4.55 (tt, J=12.2, 4.0 Hz, 1H), 3.03-2.92 (m, 2H), 2.37 (q, J=7.2 Hz, 2H), 2.11-1.98 (m, 2H), 1.89-1.78 (m, 2H), 1.55-1.38 (m, 2H), 1.02 (t, J=7.2 Hz, 3H); $^{13}$C NMR (CDCl$_3$, 75 MHz): δ 156.7 (q, J=35 Hz), 134.8, 130.6, 129.4, 128.9, 116.5 (q, J=289 Hz), 55.3, 52.4, 52.1, 29.7, 12.1. HMRS [M+H]$^+$ (C$_{15}$H$_{20}$F$_3$N$_2$O$^+$) Calcd 301.1522 Found 301.1531.

Example 47

1,1-diethyl-4-(2,2,2-trifluoro-N-phenylacetamido)piperidinium iodide (5). In a sealed vial, N-(1-ethylpiperidin-4-yl)-2,2,2-trifluoro-N-phenylacetamide (4) (417 mg, 1.39 mmol, 1 equiv) was dissolved in dry THF; after addition of copper as a stabilizer, EtI (782 μL, 7 equiv) was added and the resulting mixture was heated at 90° C. until complete consumption of the starting material (22 h, TLC in CH$_2$Cl$_2$/MeOH 95/5). Upon completion, the mixture was cooled to room temperature and the solvent removed in vacuo. The crude was then purified by chromatography (silica column, elution in CH$_2$Cl$_2$/MeOH 94/6 to 9/1) to afford purified 5 as a yellow solid (520 mg, yield 82%). m.p.=141.0-142.0° C.; R$_f$=0.4 in CH$_2$Cl—/MeOH 75/25; $^1$H NMR (CD$_3$OD, 300 MHz): δ 7.58-7.46 (m, 3H), 7.46-7.33 (m, 2H), 4.69-4.53 (m, 1H), 3.72-3.59 (m, 2H), 3.53-3.21 (m, 6H), 2.25-1.97 (m, 4H), 1.32 (t, J=6.4 Hz, 3H), 1.22 (t, J=7.4 Hz, 3H); $^{13}$C NMR (DMSO-d6, 75 MHz): δ 155.4 (q, J=34 Hz), 134.9, 130.0, 129.8, 129.2, 115.9 (q, J=289 Hz), 57.4, 56.0, 54.9 (CH$_2$Cl$_2$), 53.2, 47.3, 22.7, 7.1, 6.7. HMRS [M] (C$_{17}$H$_{24}$F$_3$N$_2$O$^+$) Calcd 329.1835 Found 329.1849.

Example 48

1,1-diethyl-4-(phenylamino)piperidinium iodide (6). In a round-bottom flask flushed with argon, 1,1-diethyl-4-(2,2,2-trifluoro-N-phenylacetamido)piperidinium iodide (5) (400 mg, 0.88 mmol, 1 equiv) was dissolved in MeOH/water 7/1 (49/7 mL); K$_2$CO$_3$ (1.46 g, 10.56 mmol, 12 equiv) was added at room temperature and the resulting mixture was then heated at 65° C. until completion (1 h, TLC CH$_2$Cl$_2$/MeOH 9/1). The mixture was then cooled to room temperature and the solvents were removed under vacuum. The crude was dissolved in MeOH and filtered through cotton to remove precipitates, and the filtered solution was concentrated in vacuo. Purification on a silica column (CH$_2$Cl$_2$/MeOH 9/1 to 85/15) afforded the pure compound as a light yellow solid (173 mg), which was then crystallized from hot ethanol to obtain white crystals, (79 mg, 25%); m.p.=203-204° C.; R$_f$=0.37 in CH$_2$Cl$_2$/MeOH 75/25; $^1$H NMR (CD$_3$OD, 500 MHz): δ 7.12 (t, J=7.5 Hz, 2H), 6.71 (d, J=7.9 Hz, 2H), 6.65 (t, J=7.4 Hz, 1H), 3.76-3.68 (m, 1H), 3.63-3.56 (m, 2H), 3.50 (q, J=7.1 Hz, 2H), 3.46-3.36 (m, 4H), 2.25-2.15 (m, 2H), 1.94-1.83 (m, 2H), 1.35 (t, J=7.3 Hz, 3H), 1.31 (t, J=8.0 Hz, 3H); $^{13}$C NMR (DMSO-d6, 75 MHz): δ 147.2, 129.1, 116.3, 112.8, 55.6, 55.0, 49.5, 45.4, 25.0, 7.2, 6.7. HMRS [M]$^+$ (C$_{15}$H$_{25}$N$_2^+$) Calcd 233.2012 Found 233.2010.

Example 49

4-benzylidene-1-ethylpiperidine (7). In a flame-dried and argon-flushed roundbottom flask, to a solution of diethyl benzylphosphonate (1.2 mL, 1.27 g, 5.57 mmol, 1.5 equiv) and 15-crown-5 (150 μL, 167 mg, 0.76 mmol, 0.2 equiv) in dry THF (17 mL) at 0° C. was added sodium hydride 60% dispersion in mineral oil (223 mg, 5.57 mmol, 1.5 equiv, portion-wise addition). After stirring 40 min at 0° C., a solution of 1-ethyl-4-piperidone (500 μL, 472 mg, 3.71 mmol, 1 equiv) in dry THF (30 mL) was added dropwise at 0° C. After stirring at 0° C. for 10 min, the reaction mixture was allowed to warm up and stir at room temperature until completion (TLC in CH$_2$Cl$_2$/MeOH 9/1), which occurred after 4 days. The mixture was cooled to 0° C., diluted with deionized water, and then the product was extracted three times with EtOAc. The organic layer was washed with saturated aqueous NaHCO$_3$ and saturated brine, then dried over MgSO$_4$. The solvent was removed under reduced pressure to yield a yellow oil that was purified on a silica gel column (CH$_2$Cl$_2$/MeOH 96/4) to afford the desired product as a pale yellowish oil (337 mg, 45% yield). R$_f$=0.33 in CH$_2$Cl$_2$/MeOH 85/15; $^1$H NMR (CD$_3$OD, 300 MHz): δ 7.33-7.26 (m, 2H), 7.21-7.15 (m, 3H), 6.35 (s, 1H), 2.65 (dd, J=6.5, 5.1 Hz, 2H), 2.58-2.49 (m, 6H), 2.48-2.42 (m, 2H), 1.15 (t, J=7.3 Hz, 3H); $^{13}$C NMR (CD$_3$OD, 75 MHz): δ 139.2, 138.8, 129.9, 129.2, 127.4, 125.1, 55.7, 54.9, 53.2, 36.4, 29.3, 11.8.

Example 50

4-benzylidene-1,1-diethylpiperidinium iodide (8). In a sealed vial, 4-benzylidene-1-ethylpiperidine (7) (337 mg, 1.67 mmol, 1 equiv) was dissolved in EtOH; after addition of some copper metal as stabilizer, EtI (940 μL, 7 equiv) was added and the resulting mixture was heated at 90° C. until complete consumption of the starting material (TLC in CH$_2$Cl$_2$/MeOH 9/1). Upon completion (51 h), the mixture was cooled to room temperature and the solvent removed in vacuo. The crude was then purified by a silica gel column eluting with CH$_2$Cl$_2$/MeOH 95/5 to 75/25; the product was then further purified by a second silica column using the same eluent and by crystallization in ethanol/methanol 1:1, affording 18 mg of pure product (3%) as white crystals. m.p.=84.5-86.0° C.; R$_f$=0.34 in CH$_2$Cl$_2$/MeOH 8/2; $^1$H NMR (CD$_3$OD, 300 MHz): δ 7.41-7.30 (m, 2H), 7.30-7.20 (m, 3H), 6.59 (s, 1H), 3.51 (q, J=7.1 Hz, 6H), 3.41-3.34 (m, 2H), 2.91-2.81 (m, 2H), 2.81-2.73 (m, 2H), 1.34 (tt, J=7.3, 1.9 Hz, 6H); $^{13}$C NMR (CD$_3$OD, 126 MHz): δ 137.6, 132.2, 129.9, 129.5, 128.7, 128.2, 59.9, 59.2, 54.1, 30.3, 24.1, 7.5. HMRS [M]$^+$ (C$_{16}$H$_{24}$N$^+$) Calcd 230.1903 Found 230.1900.

Example 50

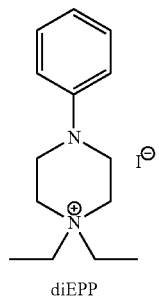

diEPP

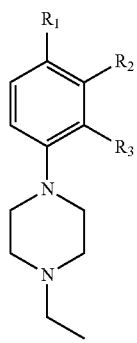
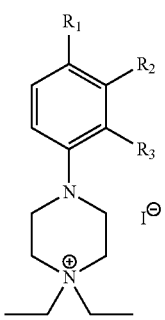
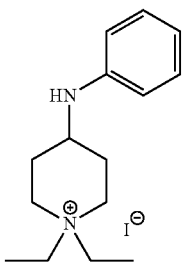

1m (R = H)
2m (R = Et)

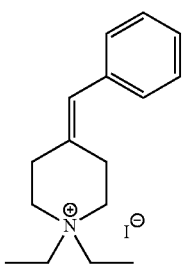

TABLE 3

| Compound | | R₁ | R₂ | R₃ |
|---|---|---|---|---|
| 1a | 2a | CH₃ | H | H |
| 1b | 2b | CN | H | H |
| 1c | 2c | OCH₃ | H | H |
| 1d | 2d | H | CH₃ | H |
| 1e | 2e | Cl | H | H |
| 1f | 2f | H | Cl | H |
| 1g | 2g | H | OCH₃ | H |
| 1h | 2h | H | H | CH₃ |
| 1i | 2i | H | CN | H |
| 1j | 2j | H | H | Cl |
| 1k | 2k | H | OH | H |
| 1l | 2l | OCH₃ | H | OCH₃ |
| 1n | 2n | CF₃ | H | H |
| 1o | 2o | H | CF₃ | H |
| 1p | 2p | H | Br | H |
| 1q | 2q | Br | H | H |
| 1r | 2r | F | H | H |
| 1s | 2s | H | F | H |
| | 2t | CONH₂ | H | H |
| | 2u | H | CONH₂ | H |

Example 51

Figure 5:
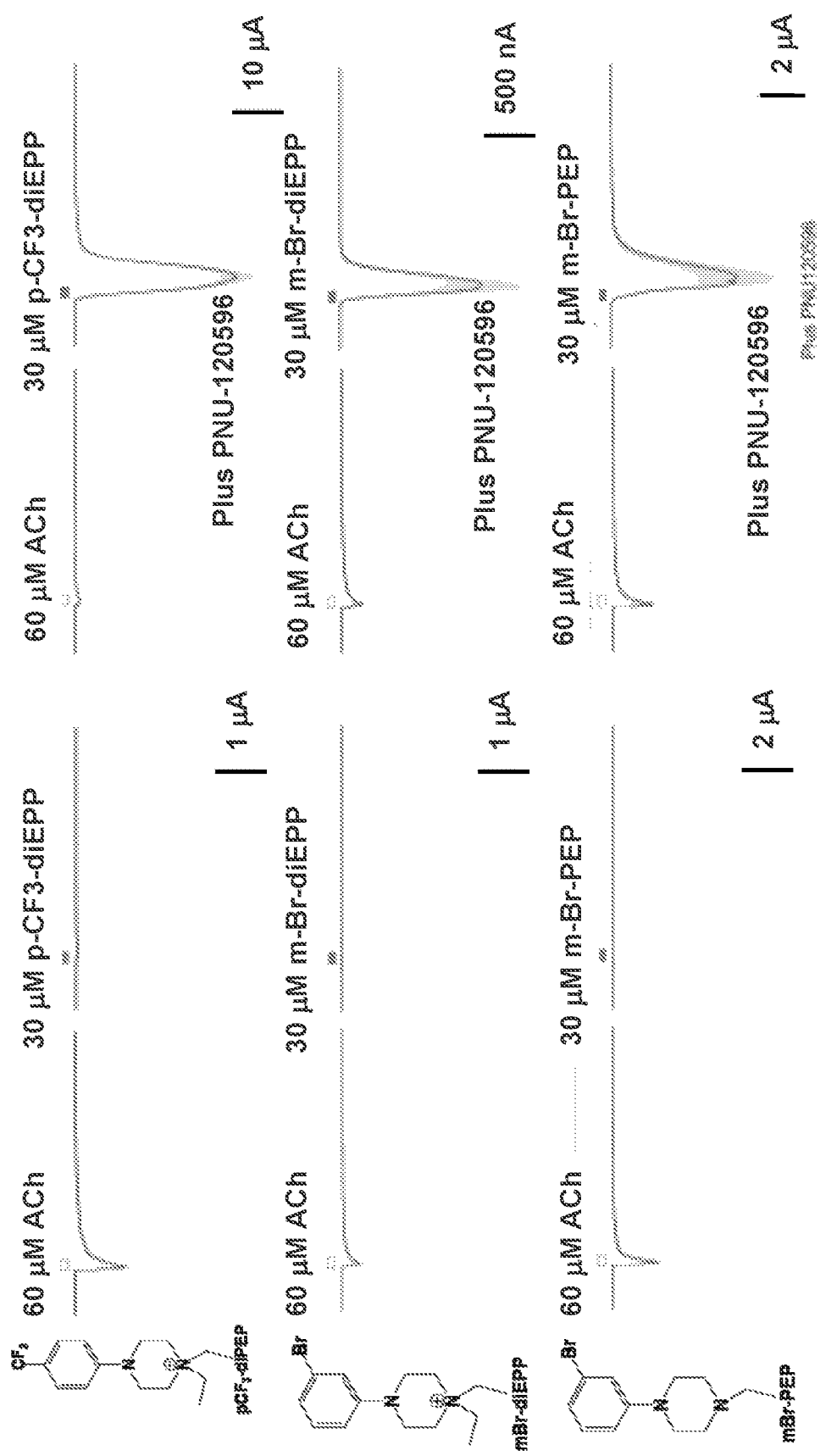
FIG. 5 illustrates that silent agonists have low efficacy for activating the α7 ion channel when applied alone but induce desensitized states that can be converted to active states with a positive allosteric modulator like PNU-120596.
Figure 6:
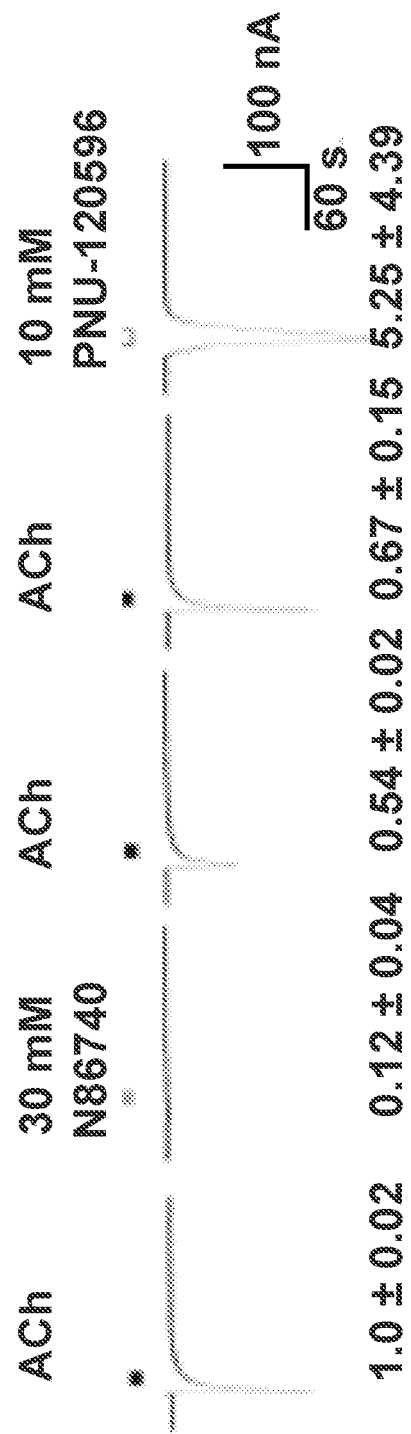
FIG. 6 illustrates that the silent agonist NS6740 induces a desensitized state that can be converted to an active state with a positive allosteric modulator like PNU-120596.
Figure 7:
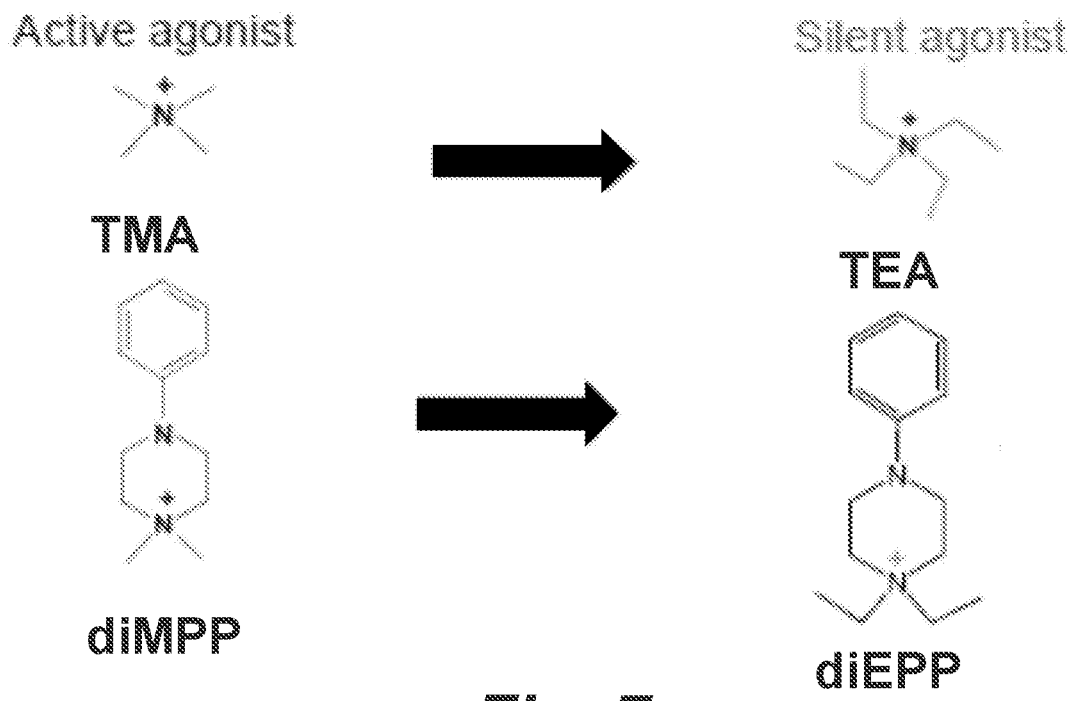
FIG. 7 illustrates the minimal pharmacophore for silent agonism of the α7 nicotinic acetylcholine receptor (nAChR).
Figure 8:
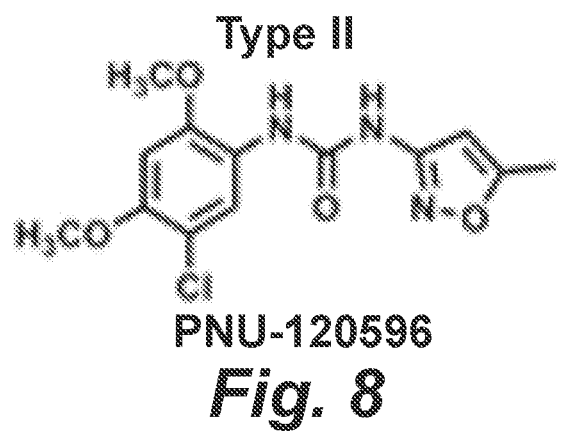
FIG. 8 illustrates the structure of the type II PAM of α7 nAChR, PNU-120596.
Figure 9:
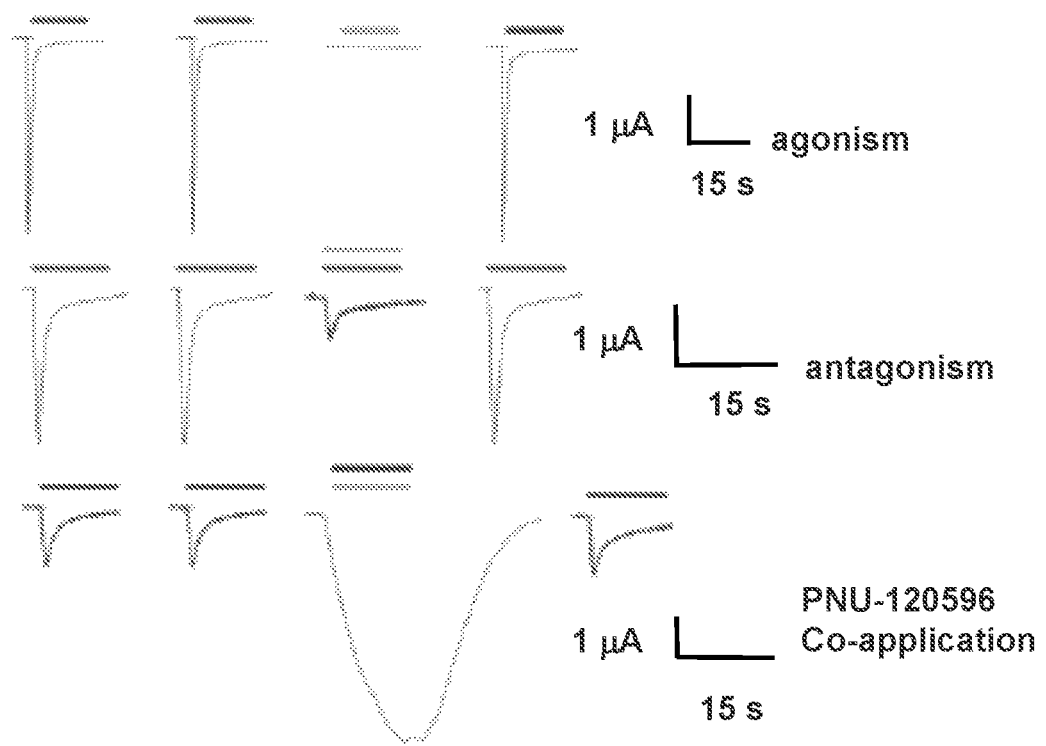
FIG. 9 illustrates representative traces of the hα7 nAChR response to the application of a silent agonist and PNU-120596.
Figure 10:
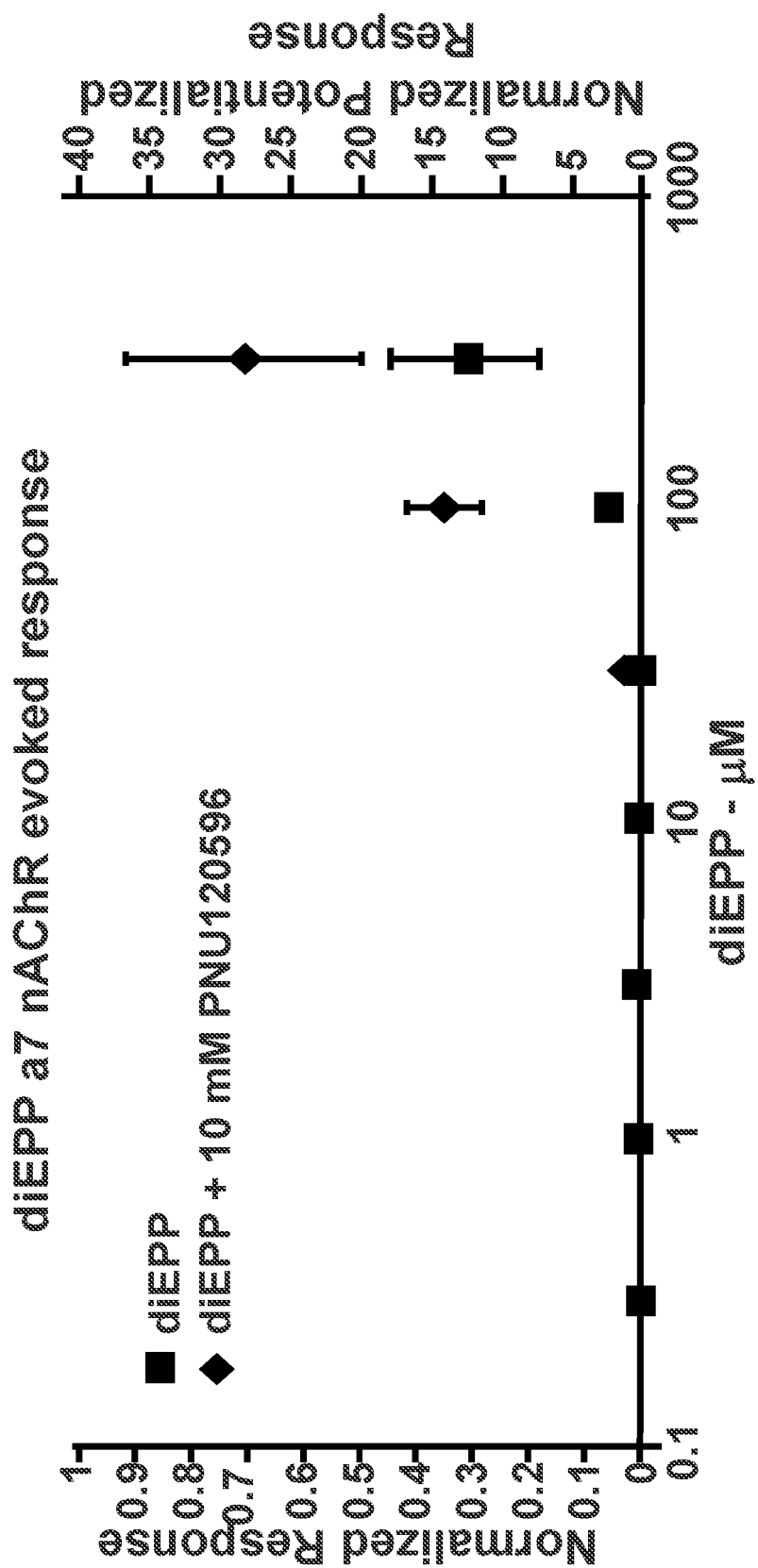
FIG. 10 is a graph illustrating the net-charge responses of oocytes expressing human α7 receptors for diEPP.
Figure 11:
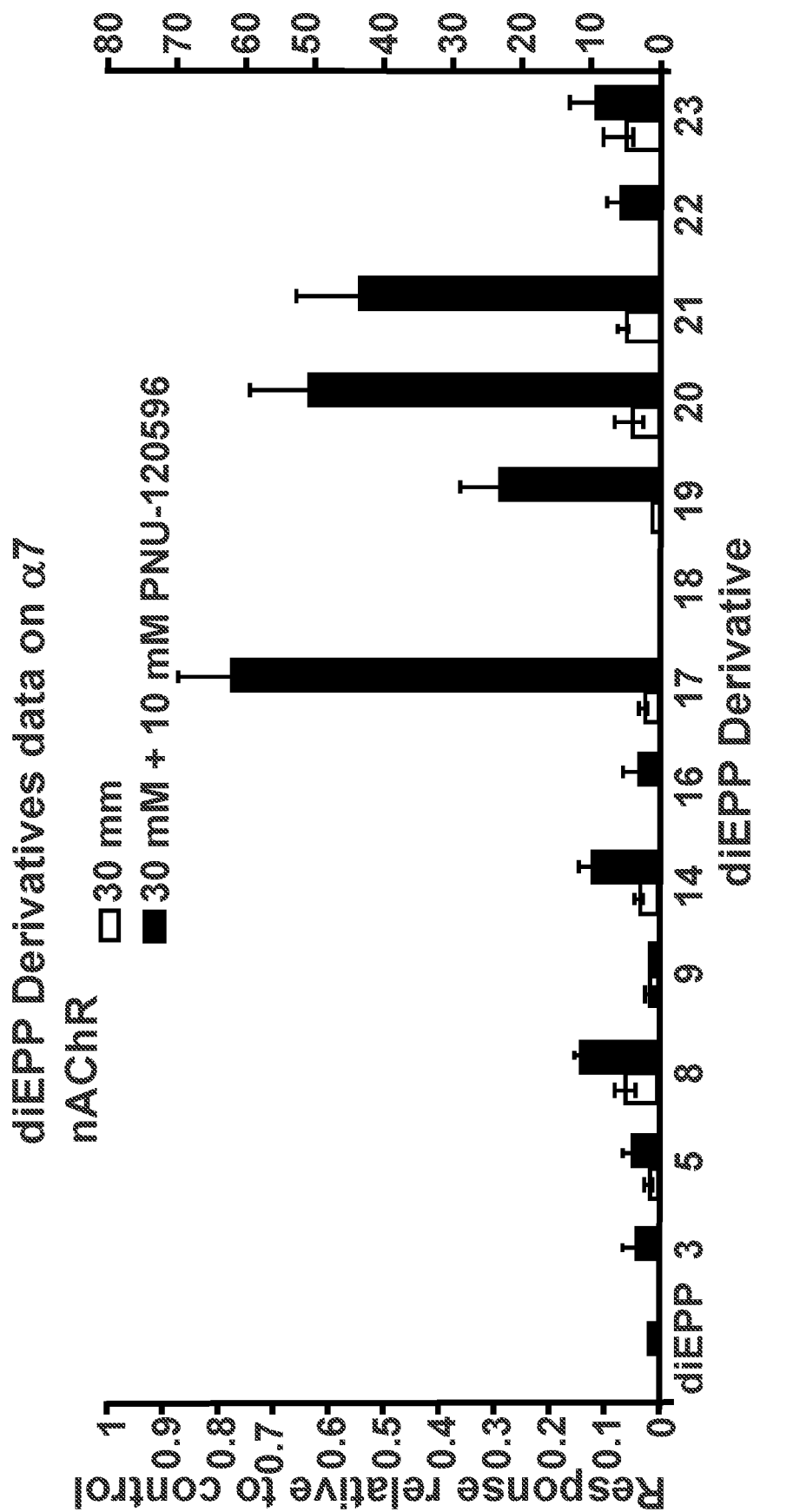
FIG. 11 is a graph illustrating the net-charge responses of oocytes expressing human α7 receptors for diEPP derivatives found to silent agonists. diEPP derivatives were tested in one shot experiments at 30 μM, with 60 μM ACh as control.

Electrophysiology: New compounds were assayed for activity with the α7 nAChR expressed in *Xenopus* oocytes using two-electrode voltage clamping as previously described in Papke et al., (2014) *J. Pharmacol. Experimental Therap.* 350: 665-680, incorporated herein by reference in its entirety, and compared to responses evoked by 60 μM Ach (FIGS. 5 and 6). The compound set was assayed at a concentration of 30 μM to provide a standard comparison benchmark.

Based on earlier experience this concentration is high enough to provide an observable response and low enough to avoid possible complications such as channel block. The net-charge response for each compound application is reported relative to those for ACh control applications. Data were expressed as the mean±S.E.M. from at least four oocytes for each experiment and were plotted by Kaleidagraph (Abelbeck Software, Reading, Pa.).

TABLE 1

Compounds tested in this study.

| Compound | Relative response[a] | Potentiated response[a] |
|---|---|---|
| diEPP | 0.002 ± 0.003 | 1.3 ± 0.3 |
| 1f, m-chloro PEP | 0.009 ± 0.008 | 0.1 ± 0.1 |
| 1n, p-CF3 PEP | 0.000 ± 0.004 | 1.4 ± 0. |
| 1p, m-bromo PEP | 0.000 ± 0.003 | 6.9 ± 2.4 |
| 1r, p-fluoro PEP | 0.000 ± 0.003 | 0.0 ± 0.0 |
| 2a, p-methyl | 0.011 ± 0.003 | 3.6 ± 2.0 |
| 2b, p-cyano | 0.234 ± 0.024 | 68.0 ± 25.4 |
| 2c, p-methoxy | 0.063 ± 0.014 | 11.6 ± 0.3 |
| 2d, m-methyl | 0.001 ± 0.000 | 0.2 ± 0.1 |
| 2e, p-chloro | 0.234 ± 0.048 | 18.3 ± 6.2 |
| 2f, m-chloro | 0.020 ± 0.003 | 4.2 ± 1.0 |
| 2g, m-methoxy | 0.011 ± 0.011 | 0.6 ± 0.2 |
| 2h, o-methyl | 0.319 ± 0.066 | 16.4 ± 2.4 |
| 2i, m-cyano | 0.022 ± 0.024 | 1.5 ± 0.7 |
| 2j, o-chloro | 0.367 ± 0.054 | 36.6 ± 6.1 |
| 2k, m-OH | 0.283 ± 0.013 | 31.4 ± 5.1 |
| 2l, p,o-dimethoxy | 0.014 ± 0.009 | 1.1 ± 0.1 |
| 2m, 2-naphthalene | 0.143 ± 0.018 | 15.9 ± 2.3 |
| 2n, p-CF3 | 0.032 ± 0.003 | 61.8 ± 7.7 |
| 2o, m-CF3 | 0.000 ± 0.002 | 3.1 ± 2.1 |
| 2p, m-bromo | 0.040 ± 0.006 | 10.0 ± 1.7 |

TABLE 1-continued

Compounds tested in this study.

| Compound | Relative response[a] | Potentiated response[a] |
|---|---|---|
| 2q, p-bromo | 0.270 ± 0.017 | 12.3 ± 3.5 |
| 2r, p-fluoro | 0.010 ± 0.002 | 22.9 ± 5.8 |
| 2s, m-fluoro | 0.061 ± 0.089 | 0.2 ± 0.1 |
| 2t, p-CONH$_2$ | 0.065 ± 0.009 | 43.9 ± 8.5 |
| 2u, m-CONH$_2$ | 0.056 ± 0.022 | 50.7 ± 8.5 |
| 6, diEPP analogue | 0.002 ± 0.004 | 5.6 ± 2.1 |
| 8, diEPP analogue | 0.071 ± 0.027 | 9.9 ± 3.1 |

[a]Values are the mean ± SEM for N ≥ 4 experiments. All data are relative to the response of the receptor to 60 μM control applications of ACh. "Relative response" refers to receptor response to a 30 μM application of test compound. Potentiated response refers to receptor response with 30 μM test compound and 10 μM PNU-120596 co-application.

TABLE 2

Partial agonist properties

| Compound | Peak current[a] | Net Charge[a] | Ratio | Estimated Rank potency | Estimated Rank efficacy | PNU Response[a] |
|---|---|---|---|---|---|---|
| o-chloro(2j) | 0.23 ± 0.03 | 0.37 ± 0.05 | 0.63 | 4 | 2 | 37 ± 6 |
| o-methyl(2h) | 0.15 ± 0.02 | 0.32 ± 0.07 | 0.46 | 5 | 1 | 16 ± 2 |
| m-hydroxy(2k) | 0.19 ± 0.02 | 0.28 ± 0.02 | 0.67 | 3 | 4 | 31 ± 5 |
| naphthalene(2m) | 0.10 ± 0.02 | 0.14 ± 0.02 | 0.71 | 1 | 6 | 16 ± 2 |
| p-chloro(2e) | 0.17 ± 0.02 | 0.23 ± 0.05 | 0.71 | 1 | 5 | 18 ± 6 |
| p-cyano(2b) | 0.10 ± 0.01 | 0.23 ± 0.02 | 0.43 | 6 | 3 | 68 ± 25 |

[a]Relative to 60 μM ACh controls (n ≥ 4)

Example 52

Synthesis of Para-Pentafluorosulfanyl diEPP (Bromine Salt) (5.MQ.65):

The present compound was synthesized according to the procedure as shown in FIG. 1. 1-ethylpiperazine (1.5 equiv) was reacted with 4-bromophenylsulfur pentafluoride (1 equiv), K$_3$PO$_4$ (2 equiv), CuI (0.1 equiv) and L-proline (0.2 equiv) in DMSO at 90-100° C. for 17 h to give 5.MQ.65. (b) EtBr 10 equiv., dry THF, 80-90° C., 118 h to give 5.MQ.67.

Example 53

Synthesis of Cyclohexil diEPP (2.MQ.173.2):

1-phenylpiperazine hydrochloride was dissolved in NaOH 1M and the aqueous phase was extracted five times with diethyl ether to give, after evaporation of the solvent, 1-phenylpiperazine as free base. 1-phenylpiperazine was dissolved in CH$_3$CN, K$_2$CO$_3$ (1.5 equiv) was added, followed by 1,5-diiodopentane (1 equiv). The reaction mixture was heated and stirred at 75° C. for 2 h. After evaporation of the solvent, the crude mixture was purified over a silica gel column chromatography, eluting in CH$_2$Cl$_2$/MeOH 95:5 to 8:2. The isolated product was then re-crystalized from a mixture of THF/EtOH/MeOH to give 2.MQ.173.2 having the formula:

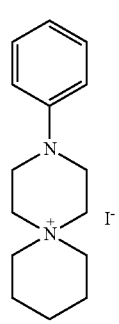

2.MQ.173.2

We claim:

1. A compound having the formula I:

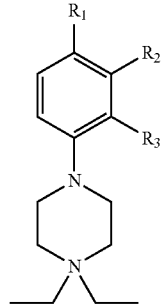

I or a pharmaceutically acceptable salt thereof, wherein:
R$_1$ and R$_2$ are each hydrogen and R$_3$ is trihaloalkyl,
R$_1$ and R$_3$ are each hydrogen and R$_2$ is trihaloalkyl, or
R$_2$ and R$_3$ are each hydrogen and R$_1$ is trihaloalkyl.

2. The compound of claim 1, wherein the trihaloalkyl is trifluoromethyl.

3. A pharmaceutical composition comprising a compound having the formula I:

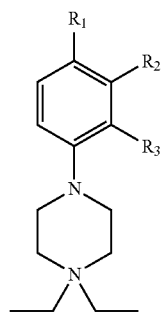

I or a pharmaceutically acceptable sail thereof, wherein:
R$_1$ and R$_2$ are each hydrogen and R$_3$ is trihaloalkyl,
R$_1$ and R$_3$ are each hydrogen and R$_2$ is trihaloalkyl, or
R$_2$ and R$_3$ are each hydrogen and R$_1$ is trihaloalkyl; and
a pharmaceutically acceptable carrier.

4. The compound of claim 2, wherein the trihaloalkyl is trifluoromethyl.

* * * * *